United States Patent [19]

O'Reilly et al.

[11] Patent Number: 5,854,205
[45] Date of Patent: Dec. 29, 1998

[54] THERAPEUTIC ANTIANGIOGENIC COMPOSITIONS AND METHODS

[75] Inventors: Michael S. O'Reilly, Winchester; M. Judah Folkman, Brookline, both of Mass.

[73] Assignee: The Children's Medical Center Corporation, Boston, Mass.

[21] Appl. No.: 740,168

[22] Filed: Oct. 22, 1996

Related U.S. Application Data

[60] Provisional application Nos. 60/005,835 Oct. 23, 1995, 60/023,070 Aug. 2, 1996 and 60/026,263 Sep. 17, 1996.

[51] Int. Cl.$^6$ .......................... A01N 61/00; A61K 38/00; C12P 21/06; G01N 33/574

[52] U.S. Cl. .............................. 514/2; 530/326; 435/69.1; 435/7.23

[58] Field of Search ................................. 530/350, 326; 514/2; 435/69.1, 7.23

[56] References Cited

FOREIGN PATENT DOCUMENTS

| 58036391 | 3/1983 | Japan . |
|---|---|---|
| WO 91/10424 | 7/1991 | WIPO . |
| WO 93/16716 | 9/1993 | WIPO . |
| WO 95/25543 | 9/1995 | WIPO . |
| WO 95/29242 | 11/1995 | WIPO . |

OTHER PUBLICATIONS

Algire, G.H. et al., "Vascular reactions of normal and malignant tumors in vivo. I. Vascular reactions of mice to wounds and to normal and aneoplastic transplants", *J. Natl. Canc. Inst.*, vol. 6, pp. 73–85 (1945).

Chen, C. et al., "A Strategy to Discover Circulating Angiogenesis Inhibitors Generated by Human Tumors", *Canc Resch.*, vol. 55, pp. 4230–4233 (1995).

Grant, D.S. et al., "Scatter factor induces blood vessel formation in vivo", *Proc. Natl. Acad. Sci. USA*, vol. 99, pp. 1937–1941 (1993).

Muragaki, Y. et al., "Mouse col 18a1 is expressed in a tissue–specific manner as three alternative variants and is localized in basement membrane zones", *Proc. Natl. Acad. Sci. USA*, vol. 92, pp. 8763–8767 (1995).

Studier, W.F. et al., "Use of T7 RNA polymerase to direct expression of cloned genes", *Methods Enzymol.*, vol. 185, pp. 60–89 (1990).

Abe et al. Biochem. Biophys Res Comm. 196:576–582, Oct. 1993.

Oh et al. ProC. Natl. Acad. Sci. USA 91:4229–33, May 1994.

Rehn et al. J. Biol. Chem. 269:13929–35, May 13, 1994.

Drug News 3:482 May 9, 1997, 1990.

Abe, N. et al., "Identification of a Novel Collagen Chain Represented by Extensive Interruptions in the Triple–Helical Region", *Biochem. and Biophy. Resch. Comm.*, vol. 196, No. 2, pp. 576–582 (1993).

Angiolillo, A.I. et al., "Human interferon–inducible Protein 10 is a potent inhibitor of angiogenesis in vivo", *J. Exp. Med.*, vol. 182, pp. 155–162 (1995).

Brem, H. et al., "Interstitial chemotherapy with drug polymer implants for the treatment of recurrent gliomas", *J. Neurosurg.*, vol. 74, pp. 441–446 (1991).

Brockway, W.J. et al., "Measurement of the Binding of Antifibrinolytic Amino Acids to Various Plasminogens", *Arch. Biochem. Biophys.*, vol. 151, pp. 194–199 (1972).

(List continued on next page.)

*Primary Examiner*—Sheela Huff
*Assistant Examiner*—Yvonne Eyler
*Attorney, Agent, or Firm*—Jones & Askew

[57] ABSTRACT

Isolated endostatin protein that is an inhibitor of endothelial cell proliferation and angiogenesis. Endostatin protein has a molecular weight of approximately 18 kDa as determined by non-reducing gel electrophoresis or approximately 20 kDa as determined by reducing gel electrophoresis. Endostatin protein corresponds to a C-terminal fragment of collagen type XVIII, and the protein can be isolated from the murine hemangioendothelioma EOMA cell line.

34 Claims, 16 Drawing Sheets

OTHER PUBLICATIONS

Browne, M.J. et al., "Expression of Recombinant Human Plasminogen and Aglycoplasminogen in HeLa Cells", *Fibrinolysis*, vol. 5, pp. 257–260 (1991).

Cao, Y. et al., "gro–β, α–C–X–C–Chemokine, Is an Angiogenesis Inhibitor That Suppresses the Growth of Lewis Lung Carcinoma in Mice", *J. Exp. Med.*, vol. 182, pp. 2069–2077 (1995).

Clapp, C. et al., "The 16–kilodalton N–terminal fragment of human prolactin is a potent inhibitor of angiogenesis", *Endocrinology*, vol. 133, pp. 1292–1299 (1993).

Cleary, S. Mulkerrin et al., "Purification and Characterization of Tissue Plasminogen Activator Kringle–$^2$ Domain Expressed in *Escherichia coli*", *Biochem.*, vol. 28, pp. 1884–1891 (1989).

Dameron, K.M. et al., "Control of angiogenesis in fibroblasts by p53 regulation of thrombospondin–1", *Science*, vol. 265, pp. 1585–1584 (1994).

Folkman, J., "Tumor angiogenesis and tissue factor", *Nature Med.* vol. 2, pp. 167–168 (1996).

Folkman, J., "What is the Evidence that Tumors are Angiogenesis Dependent?", *J. Natl Canc Inst.*, vol. 82, pp. 4–6 (1990).

Folkman, J., "Angiogenesis in cancer, vascular, rheumatoid and other disease", *Nature Medicine*, vol. 1, No, 1, pp. 27–31 (1995).

Folkman, J., "Long–term culture of capillary endothelial cells", *Proc. Natl. Acad. Sci. USA* 76, pp. 5217–5221 (1979).

Folkman, J. et al., "Induction of angiogenesis during the transition from hyperplasia to neoplasia", *Nature*, vol. 339, pp. 58–61 (1989).

Folkman, J. et al., "Tumor Behavior in Isolated Perfused Organs In Vitro Growth and Metastases of Biopsy Material in Rabbit Thyroid and Canine Intestinal Segment", *Annals of Surgery*, vol. 164, No. 3, pp. 491–501 (1996).

Folkman, J., "Angiogenesis and Its Inhibitors", *Important Advances in Oncology*, J.B. Lippincott Company, pp. 42–62 (1985).

Folkman, J., "Tumor Angiogenesis Therapeutic Implications", *NE J. of Med.*, No. 18, pp. 1182–1186 (1971).

Gavrieli, Y. et al., "Identification of programmed cell death in situ via specific labeling of nuclear DNA fragmentation", *J. CellBiol.*, vol. 119, pp. 493–501 (1992).

Gimbrone, M.A. et al., "Tumor Growth and Neovascularization An Experimental Model using the Rabbit Cornea", *J. Natl. Canc. Inst.*, vol. 52, No. 2 pp. 413–427 (1974).

Gimbrone, M.A. et al., "Tumor Dormancy in Vivo by Prevention of Neovascularization", *J. of Experi. Med.*, vol. 136, pp. 261–276 (1972).

Good, D.J. et al., "A tumor suppressor–dependent inhibitor of angiogenesis is immunologically and functionally indistinguishable from a fragment of thrombospondin", *Proc. Nat. Acad. Sci. USA*, vol. 87, pp. 6624–6628 (1990).

Grant, D.S. et al., "Two different laminin domains mediate the differentiation of human endothelial cells into capillary–like structures in vitro", *Cell*, vol. 58, pp. 933–943 (1989).

Gross, J.L. et al., "Modulation of Solid Tumor Growth in vivo by bFGF", *Proc. Amer. Assoc. Canc. Resh*, vol. 31, p. 79 (1990).

Gross, J.L. et al., "Increased capillary endothelial cell protease activity in response to angiogenic stimuli in vitro.", *Proc. Natl. Acad. Sci. USA*, vol. 80, pp. 2623–2627 (1983).

Gunzler, W.A. et al., "The Primary Structure of High Molecular Mass Urokinase from Human Urine", *Hoppe–Seyler's Z. Physiol. Chem.*, vol. 363, pp. 1155–1165 (1982).

Gupta, S.K. et al., "A potent inhibitor of endothelial cell proliferation is generated by proteolytic cleavage of the chemokine platelet factor 4", *Proc. Natl. Acad. Sci. USA*, vol. 92, pp. 7779–7803 (1995).

Holmgren, L. et al., "Dormancy of micrometastases Balanced proliferation and apoptosis in the presence of angiogenesis suppression", *Nature Medicine*, vol. 1, No. 2, pp. 149–153 (1995).

Homandberg, G.A. et al., "Heparin–binding fragments of fibronectin are potent inhibitors of endothelial cell growth", *Am. J. Path.*, vol. 120, pp. 327–332 (1985).

Hori, A. et al., "Suppression of Solid tumor Growth by Immunoneutralizing Monoclonal Antibody against Human Basic Fibroblast Growth Factor", *Canc. Resch.*, vol. 51, pp. 6180–6184 (1991).

Ingber, D. et al., "Synthetic analogues of fumagillin that inhibit angiogenesis and suppress tumor growth", *Nature*, vol. 348, pp. 555–557 (1990).

Johansson, J. et al., "Surfactant Protein B: Disulfide Bridges, Structural Properties, and Kringle Similarities", *Biochem.*, vol. 30, pp. 6917–6921 (1991).

Kandel, J. et al., "Neovascularization is Associated with a Switch to the Export of bFGF in the Multistep Development of Fibrosarcoma", *Cell*, vol. 66, pp. 1095–1104 (1991).

Kim, K.J. et al., "Inhibition of vascular endothelial growth factor–induced angiogenesis suppresses tumor growth in vivo", *Nature*, vol. 362, pp. 841–844 (1993).

Kivirikko, S. et al., "Primary Structure of the α1 Chain of Human Type XV Collagen and Exon–Intron Organization in the 3' Region of the Corresponding Gene", *J. Bio. Chem.*, vol. 269, No. 7, pp. 4773–4779 (1994).

Knighton, D. et al., "Avascular and Vascular Phases of Tumor Growth in the Chick Embryo", *Br. J. Cancer*, vol. 35, pp. 347–356 (1977).

Lein, W. M. et al., "The blood supply of experimental liver metastases. II. A Microcirculatory study of the normal and tumor vessels of the liver with the use of perfused silicone rubber", *Surgery*, vol. 68, No. 2, pp. 334–340 (1970).

Lerch et al., "Localization of Individual Lysine–Binding Regions in Human Plasminogen and Investigations on Their Complex–Forming Properties", *European Journal of Biochemistry*, vol. 107, No. 1, pp. 7–13 (19980).

Lokker, N.A. et al., "Mutational analysis and molecular modeling of the N–terminal kringle–containing domain of hepatocyte growth gactor identifies amino acid side chains important for interaction with the c–met receptor", *Prot. Engin.*, vol. 7, pp. 895–903 (1994).

Maione, T.E. et al., "Inhibition of Angiogenesis by Recombinant Human Platelet Factor–4 and Related Peptiddes", *Science*, vol. 247, pp. 77–79 (1990).

Marti, D. et al., "Expression, purification and characterization of the recOmbinant kringle 2 and kringle 3 domains of human plasminogen and analysis of their binding affinity for ω–aminocarboxylic acids", *Eur. J. Biochem.*, vol. 219, pp. 455–462 (1994).

McLean, J.W. et al., "cDNA sequence of human apolipoprotein(a) is homologous to plasminogen", *Nature*, vol. 330, pp. 132–137 (1987).

Menhart, N. et al., "Construction, Expression, and Purification of Recombinant Kringle 1 of Human Plasminogen and Analysis of Its Interaction with ω–Amino Acids", *Biochem.*, vol. 30, pp. 1948–1957 (1991).

Millauer, B. et al., "Glioblastoma growth inhibited in vivo by a dominant–negative Flk–1 mutant", *Nature*, vol. 367, pp. 576–579 (1994).

Moses, M.A. et al., "Identification of an Inhibitor of Neovascularization from Cartilage", *Science*, vol. 248 (1990).

Nelson, J.A. et al., "Murine epidermal growth factor (EGF) fragment (33–42) inhibits both EGF–and Laminin–dependent endothelial cell motility and angiogenesis", *Canc. Resch.*, vol. 55, pp. 3772–3776 (1995).

Nguyen, M. et al., "Quantitation of Angiogenesis and Antiangiogenesis in the Chick Embryo Chorioallantoic Membrane", *Microvascular Research*, vol. 47, pp. 31–49 (1994).

Nguyen, M. et al., "Elevated Levels of the Angiogenic Peptide Basic Fibroblast Growth Factor in Urine of Bladder Cancer Patients", *J. of Nat. Canc. Inst.*, vol. 85, No. 3, pp. 241–242 (1993).

O'Reilly et al., "Endogenous Inhibitors of Angiogenesis", *Proc. Am. Assoc. Canc. Resch.*, vol. 37, p. 669 (1996).

O'Reilly et al., "Angiostatin induces and sustains dormancy of human primary tumors in mice", *Nature Medicine*, vol. 2, No. 6, pp. 689–692 (1996).

O'Reilly et al., "The suppression of Tumor Metastases by a Primary Tumor", *Surgical Forum*, vol. XLIV, pp. 474–476 (1993).

O'Reilly et al., "Angiostatin A Novel Angiogenesis Inhibitor that Mediates the Suppression of Metastases by a Lewis Lung Carcinoma", *Cell*, vol. 79, pp. 315–328 (1994).

O'Reilly et al., "Angiostatin: A Circulating Endothelial Cell Inhibitor That Suppresses Angiogenesis and Tumor Growth", *Cold Spring Harbor Symposia on Quantitative Biology*, vol. LIX, pp. 471–482 (1994).

Obeso, J. et al., "Methods in Laboratory Investigation/A Hemangioendothelioma–Derived Cell Line Its Use as a Model for the Study of Endothelial Cell Biology", *Laboratory Investigation*, vol. 63, No. 2, p. 159 (1990).

Oh, S.K. et al., "Isolation and sequencing of cDNAs for proteins with multiple domains of Gly–Xaa–Yaa repeats identify a distinct family of collagenous proteins", *Proc. Natl. Acad. Sci. USA*, vol. 91, pp. 4229–4233 (1994).

Oh, S.P., "Cloning of cDNA and Genomic DNA Encoding Human Type VIII Collagen and Localization of the α1(XVIII) Collagen Gene to Mouse Chromosome 10 and Human Chromosome 21", *Genomics*, vol. 19, pp. 494–499 (1994).

Parangi, S. et al., "Antiangiogenic therapy of transgenic mice impairs de novo tumor growth", *Proc. Natl. Acad. Sci. USA*, vol. 93, pp. 2002–2007 (1996).

Passaniti, A. et al., "Methods in Laboratory Investigation/A Simple, Quantitative Method for Assessing Angiogenesis and Antiangiogenic Agents Using Reconstituted Basement Membrane, Heparin, and Fibroblast Growth Factor", *Lab. Invest.*, vol. 67, No. 4, pp. 519–528 (1992).

Ponting et al., "Plasminogen: a structural review", *Blood Coagulation and Fibrinolysis*, vol. 3, pp. 605–614 (1992).

Powell, J. R. et al., "Amino Acid Sequence Analysis of the Asparagine–288 Region of the Carbohydrate Variants of Human Plasminogen", *Biochem,.* vol. 22, pp. 923–927 (1983).

Rastinejad, F. et al., "Regulation of the activity of a new inhibitor of angiogenesis by a cancer suppressor gene", *Cell*, vol. 56, pp. 345–355 (1989).

Rehn, M. et al., "α1(XVIII), a collagen chain with frequent interruptions in the collagenous sequence, a distinct tissue distribution, and homology with type XV collagen", *Proc. Natl. Acad. Sci. USA*, vol. 91, pp. 4234–4238 (1994).

Rehn, M. et al., "Identification of three N–terminal ends of type XVII collagen chains and tissue–specific differences in the expression of the corresponding transcripts", *J. Biol. Chem.*, vol. 270, pp. 4705–4711 (1995).

Robbins, K.C., "The Plasminogen–Plasmin Enzyme System", *Fibrinolysis*, pp. 340–357 (1987).

Sage, E.H. et al., "Inhibition of Endothelial Cell Proliferation by SPARC is Mediated through a $Ca^{2+}$–Binding EF–Hand Sequence", *J. Cell. Biochem.*, vol. 57, pp. 127–140 (1995).

Sakamato, N. et al., "Inhibition of angiogenesis and tumor growth by a synthetic laminin peptide, $CDPGYIGSR-NH_2$" *Canc. Resch.*, vol. 51, pp. 903–906 (1991).

Sambrook, J. et al., "Expression of Cloned Genes in *Escherichia coli*", *Molecular Cloning Second Edition*, Cold Spring Harbor Laboratories Press, pp. 17.37–17.41, (1989).

Schaller, J. et al., "Structural Aspects of the Plasminogen of Various Species", *Enzyme*, 40 pp. 63–69 (1988).

Shi, G. et al., "Kringle Domains and Plasmin Denaturation", *Biochem. Biophy. Resch. Comm.*, vol. 178, No. 1, pp. 360–368 (1991).

Sottrup–Jensen, L. et al., "The Primary Structure of Human Plasminogen Isolation of Two Lysine–Binding Fragments and One Mini–Plasminogen (MW, 38,000) by Elastase- –Catalyzed–Specific Limited Proteolysis", *Prog. in Chem. Fibrinolysis and Thrombolysis*, vol. 3, pp. 191–209 (1978).

Srivastava, A. et al., "The Prognostic Significance of Tumor-ascularity in Intermediate–Thickness (0.76–4.0mm Thick) Skin Melanoma", *Am. J. of Path.*, vol. 133, No., pp. 419–424 (1988).

Strieter, R.M. et al., Interferonγ–inducible protein 10 (IP–10), a member of the C–X–C chemokine family, is an inhibitor of angiogenesis. *Biochem. Biophys. Resch. Comm.*, vol. 210, pp. 51–57 (1995).

Teicher, B.A. et al., "Potentiation of cytotoxic cancer therapies by TNP–470 alone and with other antiangiogenic agents", *Int. J. Canc.*, vol. 57, pp. 1–6 (1994).

Tolsma, S.S. et al., "Peptides derived from two separate domains of the matrix protein thrombospondin–1 have antiangiogenic activity", *J. Cell Biol.*, vol. 122, pp. 497–511 (1993).

Van Meir, E. et al., "Release of an inhibitor of angiogenesis upon induction of wild type p53 expression in glioblastoma cells", *Nature Genetics*, vol. 8, pp. 171–176 (1994).

Voest, E. E. et al., "Inhibition of Angiogenesis in Vivo by Interleukin 12", *J. Natl. Can. Inst.*, vol. 87, pp. 581–586 (1995).

Walz, D.A. et al., "Amino acid sequence of human prothrombin fragments 1 and 2", *Proc. Natl. Acad. Sci.*, vol. 74, pp. 1969–1973 (1977).

Weidner, N. et al., "Tumor Angiogenesis: A New Significant and Independent Prognostic Indicator in Early–Stage Breast Carcinoma", *J. Natl. Canc. Inst.*, vol. 84, pp. 1875–1887 (1992).

Weidner, N. et al., "Tumor Angiogenesis Correlates with Metastasis in Invasive Prostate Carcinoma", *Am. J. Path.*, vol. 143, No. 2, pp. 401–409 (1993).

Weidner, N. et al., "Tumor Angiogenesis and Metastasis— Correlation in Invasive Breast Carcinoma", *NE J. of Med.*, vol. 324, No. 1, pp. 1–8 (1991).

Wiman, B. et al., "On the Specific Interaction Between the Lysine–Binding Sites in Plasmin and Complementary Sites In $\alpha_2$–Antiplasmin and Fibrinogen", *Biochimica et Biophysica Acta.* vol. 579, pp. 142–154 (1979).

Yoshimura, T. et al., "Cloning, Sequencing, and Expression of Human Macrophage Stimulating Protein (MSP, MST1) Confirms MSP as a Member of the Family of Kringle Proteins and Locates the MSP Gene on Chromosome 3", *Laboratory of Immunobiology*, pp. 15461–15468 (1993).

THERAPEUTIC ANTIANGIOGENIC COMPOSITIONS AND METHODS

This invention was made with government support under the National Institutes of Health, grant P0-CA45548. The United States government may have certain rights in this invention.

CROSS REFERENCE TO PRIOR RELATED CASES

This application claims priority to provisional application Ser. No. 60/005,835 filed Oct. 23, 1995; provisional application Ser. No. 60/023,070 filed Aug. 2, 1996; and provisional application Ser. No. 60/026,263 filed Sep. 17, 1996. Each of the above-referenced applications is incorporated herein in its entirety.

TECHNICAL FIELD

This application relates to a novel inhibitor of angiogenesis useful for treating angiogenesis-related diseases, such as angiogenesis-dependent cancer. The invention further relates to a novel composition and method for curing angiogenesis-dependent cancer. In addition, the present invention relates to diagnostic assays and kits for endostatin measurement, to histochemical kits for localization of endostatin, to molecular probes to monitor endostatin biosynthesis, to antibodies that are specific for the endostatin, to the development of peptide agonists and antagonists to the endostatin receptor, and to cytotoxic agents linked to endostatin peptides.

BACKGROUND OF THE INVENTION

Several lines of direct evidence now suggest that angiogenesis is essential for the growth and persistence of solid tumors and their metastases (Folkman, 1989; Hori et al., 1991; Kim et al., 1993; Millauer et al., 1994). To stimulate angiogenesis, tumors upregulate their production of a variety of angiogenic factors, including the fibroblast growth factors (FGF and BFGF) (Kandel et al., 1991) and vascular endothelial cell growth factor/vascular permeability factor (VEGF/VPF). However, many malignant tumors also generate inhibitors of angiogenesis, including angiostatin and thrombospondin (Chen et al., 1995; Good et al., 1990; O'Reilly et al., 1994). It is postulated that the angiogenic phenotype is the result of a net balance between these positive and negative regulators of neovascularization (Good et al., 1990; O'Reilly et al., 1994; Parangi et al., 1996; Rastinejad et al., 1989). Several other endogenous inhibitors of angiogenesis have been identified, although not all are associated with the presence of a tumor. These include, platelet factor 4 (Gupta et al., 1995; Maione et al., 1990), interferon-alpha, interferon-inducible protein 10 (Angiolillo et al., 1995; Strieter et al., 1995), which is induced by interleukin-12 and/or interferon-gamma (Voest et al., 1995), gro-beta (Cao et al., 1995), and the 16 kDa N-terminal fragment of prolactin (Clapp et al., 1993). The only known angiogenesis inhibitor which specifically inhibits endothelial cell proliferation is angiostatin (O'Reilly et al. 1994).

Angiostatin is an approximately 38 kiloDalton (kDa) specific inhibitor of endothelial cell proliferation. Angiostatin is an internal fragment of plasminogen containing at least three of the five kringles of plasminogen Angiostatin has been shown to reduce tumor weight and to inhibit metastasis in certain tumor models. (O'Reilly et al., 1994). As it is used hereinafter, the term "angiostatin" refers to angiostatin as described above; peptide fragments of angiostatin that have endothelial cell proliferation inhibiting activity; and analogs of angiostatin that have substantial sequence homology (as defined herein) to the amino acid sequence of angiostatin, which have endothelial cell proliferation inhibiting activity.

SUMMARY OF THE INVENTION

The present invention relates to a novel protein inhibitor, and method for its use. The protein is a potent and specific inhibitor of endothelial proliferation and angiogenesis. Systemic therapy with the inhibitor causes a nearly complete suppression of tumor-induced angiogenesis, and it exhibits strong anti-tumor activity.

The inhibitory protein has a molecular weight of approximately 18,000 to approximately 20,000 Daltons (18 to 20 kDa) and is capable of inhibiting endothelial cell proliferation in cultured endothelial cells. The protein can be further characterized by its preferred N-terminal amino acid sequence, the first twenty (20) of which are as follows:

| His | Thr | His | Gln | Asp | Phe | Gln | Pro | Val | Leu |
|---|---|---|---|---|---|---|---|---|---|
| 1 | 2 | 3 | 4 | 5 | 6 | 7 | 8 | 9 | 10 |
| His | Leu | Val | Ala | Leu | Asn | Thr | Pro | Leu | Ser |
| 11 | 12 | 13 | 14 | 15 | 16 | 17 | 18 | 19 | 20 |

(SEQ ID NO:1)

A preferred endothelial cell proliferation inhibitor of the invention is a protein having the above-described characteristics, and which can be isolated and purified from the murine hemangioendothelioma cell line EOMA. This inhibitory protein has been named endostatin.

The present invention provides methods and compositions for treating diseases and processes mediated by undesired and uncontrolled angiogenesis by administering to a human or animal with the undesired angiogenesis a composition comprising a substantially purified endostatin or endostatin derivative in a dosage sufficient to inhibit angiogenesis. The present invention is particularly useful for treating or for repressing the growth of tumors. Administration of endostatin to a human or animal with prevascularized metastasized tumors prevents the growth or expansion of those tumors.

The present invention also includes diagnostic methods and kits for detection and measurement of endostatin in biological fluids and tissues, and for localization of endostatin in tissues. The diagnostic method and kit can be in any configuration well known to those of ordinary skill in the art. The present invention also includes antibodies specific for the endostatin and antibodies that inhibit the binding of antibodies specific for the endostatin. These antibodies can be polyclonal antibodies or monoclonal antibodies. The antibodies specific for endostatin can be used in diagnostic kits to detect the presence and quantity of endostatin which is diagnostic or prognostic for the occurrence or recurrence of cancer or other disease mediated by angiogenesis. Antibodies specific for endostatin may also be administered to a human or animal to passively immunize the human or animal against endostatin, thereby reducing angiogenic inhibition.

The present invention also includes diagnostic methods and kits for detecting the presence and quantity of antibodies that bind endostatin in body fluids. The diagnostic method and kit can be in any configuration well known to those of ordinary skill in the art.

The present invention also includes endostatin peptide fragments that can be labeled isotopically or with other molecules or proteins for use in the detection and visualization of endostatin binding sites with state of the art techniques, including, but not limited to, positron emission tomography, autoradiography, flow cytometry, radioreceptor binding assays, and immunohistochemistry.

These endostatin peptides also act as agonists and antagonists at the endostatin receptor, thereby enhancing or blocking the biological activity of endostatin. Such peptides are used in the isolation of the endostatin receptor.

The present invention also includes endostatin, endostatin fragments, endostatin antisera, or endostatin receptor agonists and antagonists linked to cytotoxic agents for therapeutic and research applications.

The present invention includes molecular probes for the ribonucleic acid and deoxyribonucleic acid involved in transcription and translation of endostatin. These molecular probes provide means to detect and measure endostatin biosynthesis in tissues and cells.

A surprising discovery is that various forms of recombinant endostatin protein can serve as sustained release anti-angiogenesis compounds when administered to a tumor-bearing animal. A preferred form of the sustained release compound is un-refolded recombinantly produced endostatin.

Additionally, the present invention encompasses nucleic acid sequences comprising corresponding nucleotide codons that code for the above disclosed amino acid sequence and for endostatin and endothelial cell proliferation inhibiting peptide fragments thereof.

The present invention also relates to methods of using the endostatin protein and peptide fragments, corresponding nucleic acid sequences, and antibodies that bind specifically to the inhibitor and its peptides, to diagnose endothelial cell-related diseases and disorders.

The invention further encompasses a method for identifying receptors specific for endostatin, and the receptor molecules identified and isolated thereby.

The invention also relates to a method for identifying novel enzymes capable of releasing endostatin from collagen type XVIII, and other molecules containing an endostatin amino acid sequence, and peptides thereof. Such endostatin producing enzymes are also an aspect of the invention.

An important medical method is a new form of birth control, wherein an effective amount of endostatin is administered to a female such that uterine endometrial vascularization is inhibited and embryo implantation cannot occur, or be sustained.

A particularly important aspect of the present invention is the discovery of a novel and effective method for treating angiogenesis-related diseases, particularly angiogenesis-dependent cancer, in patients, and for curing angiogenesis-dependent cancer in patients. The method unexpectedly provides the medically important result of inhibition of tumor growth and reduction of tumor mass. The method relates to the co-administration of the endostatin of the present invention and another anti-angiogenesis compound, preferrably angiostatin. Accordingly, the present invention also includes formulations containing endostatin, and optionally angiostatin, which are effective for treating or curing angiogenesis-dependent cancers.

Accordingly, it is an object of the present invention to provide a composition comprising an endostatin protein.

It is another object of the present invention to provide a method of treating diseases and processes that are mediated by angiogenesis.

It is yet another object of the present invention to provide a diagnostic or prognostic method and kit for detecting the presence and amount of endostatin in a body fluid or tissue.

It is yet another object of the present invention to provide a method and composition for treating diseases and processes that are mediated by angiogenesis including, but not limited to, hemangioma, solid tumors, leukemia, metastasis, telangiectasia psoriasis scleroderma, pyogenic granuloma, myocardial angiogenesis, plaque neovascularization, corornay collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, and placentation.

It is another object of the present invention to provide a composition for treating or repressing the growth of a cancer.

It is an object of present invention to provide a method for detecting and quantifying the presence of an antibody specific for an endostatin in a body fluid.

Still another object of the present invention is to provide a composition consisting of antibodies to endostatin that are selective for specific regions of the endostatin molecule.

It is another object of the present invention to provide a method for the detection or prognosis of cancer.

It is another object of the present invention to provide a composition for use in visualizing and quantitating sites of endostatin binding in vivo and in vitro.

It is yet another object of the present invention to provide a composition for use in detection and quantification of endostatin biosynthesis.

It is yet another object of the present invention to provide a therapy for cancer that has minimal side effects.

Still another object of the present invention is to provide a composition comprising endostatin or an endostatin peptide linked to a cytotoxic agent for treating or repressing the growth of a cancer.

These and other objects, features and advantages of the present invention will become apparent after a review of the following detailed description of the disclosed embodiments and the appended claims.

Conditioned media collected from confluent EOMA cells or base media was applied to bovine capillary endothelial cells with 1 ng/ml bFGF in a 72 hour proliferation assay. Endothelial cell proliferation was inhibited by the EOMA conditioned media. Each bar represents the mean ±SEM.

Figure 2:
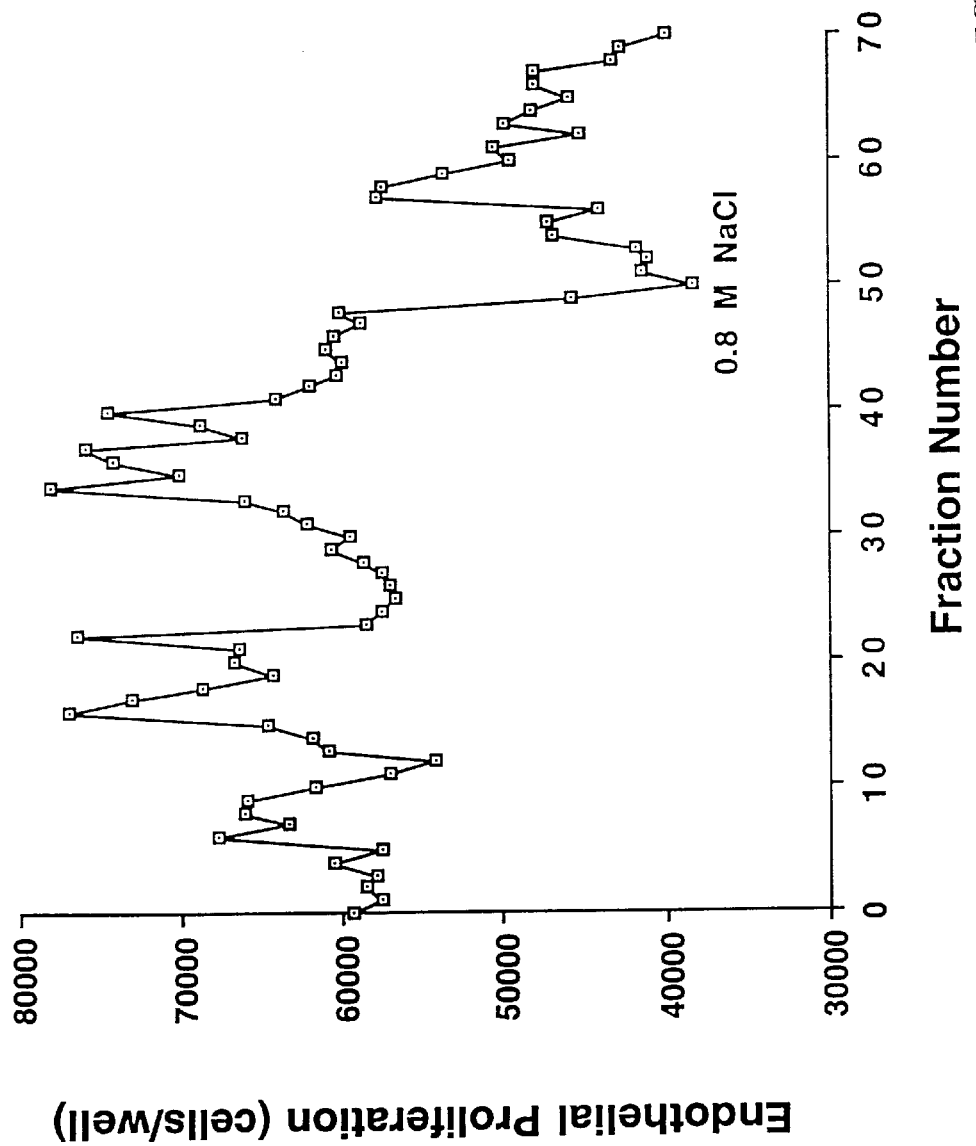

FIG. 2: Purification of an Inhibitor of Endothelial Proliferation from EOMA Conditioned Media.

Conditioned media collected from confluent EOMA cells was fractionated on a heparin sepharose column. Endothelial proliferation inhibiting activity eluted at approximately 0.8M NaCl.

Figure 3:
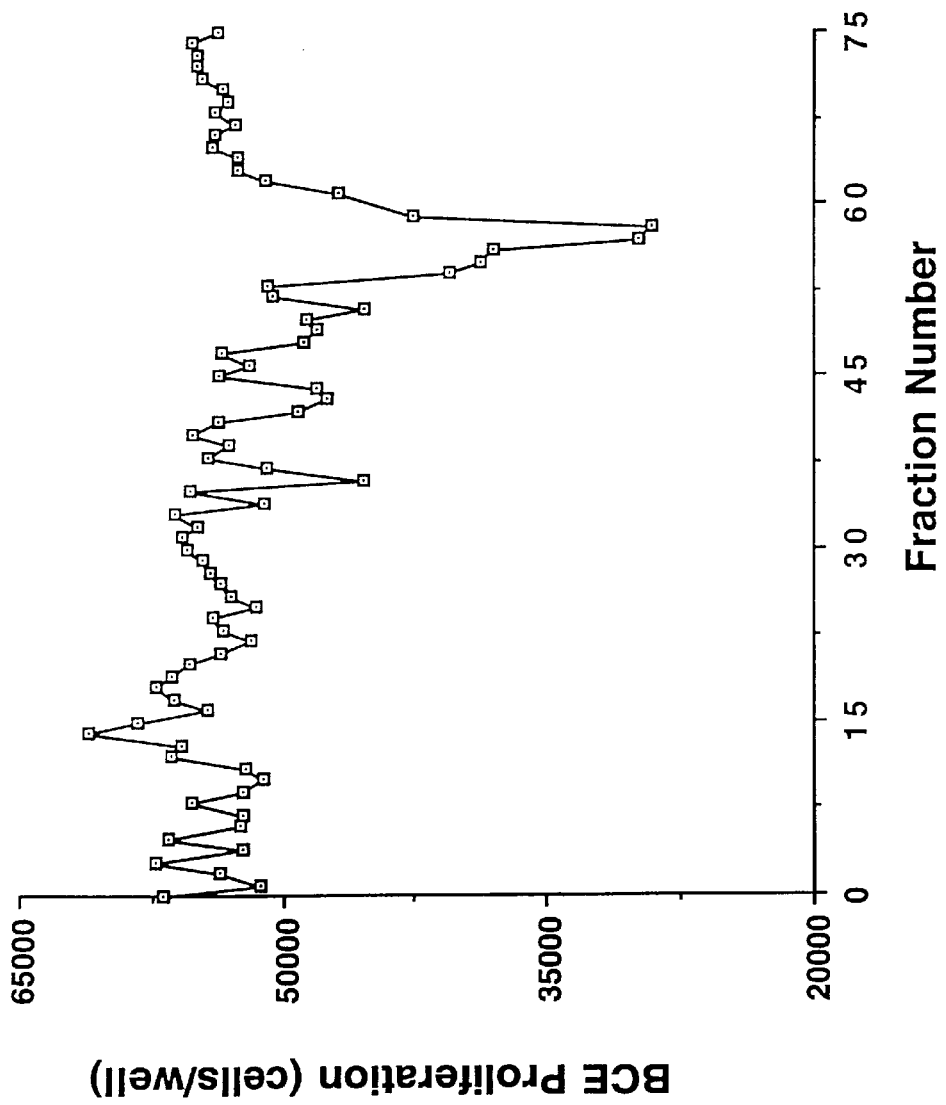

FIG. 3: Purification of an Inhibitor of Endothelial Proliferation by Gel Filtration.

Purified inhibitor from heparin sepharose column chromatography was applied to a gel filtration column and eluted as a single peak.

Figure 4:
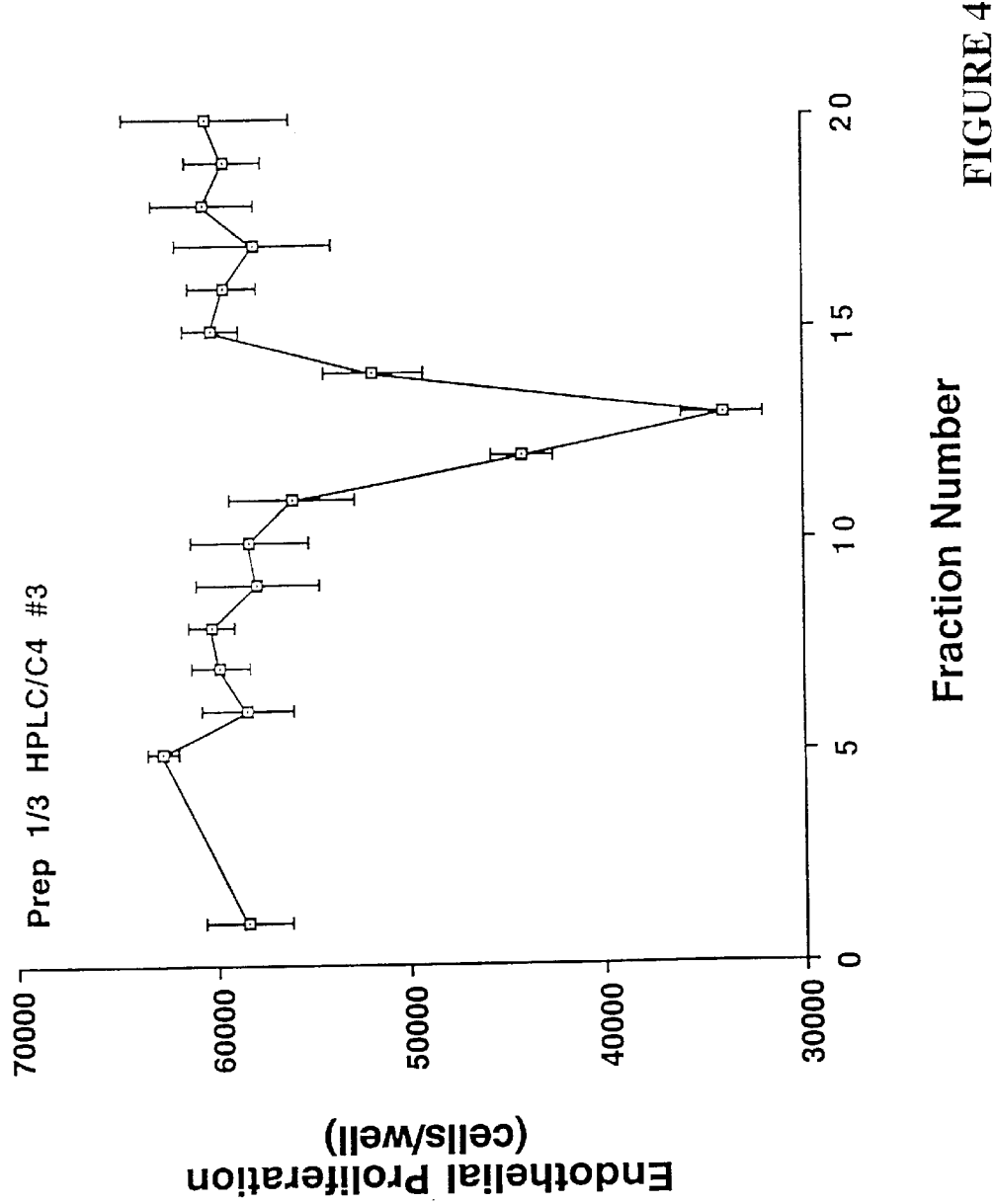

FIG. 4: Purification of Inhibitor of Endothelial Cell Proliferation by Reversed Phase Column Chromatography.

Inhibitor purified by heparin sepharose and gel filtration chromatography was applied to a reverse phase column. The inhibitor eluted as a single band from the column at approximately 45% of the acetonitrile.

Figure 5:
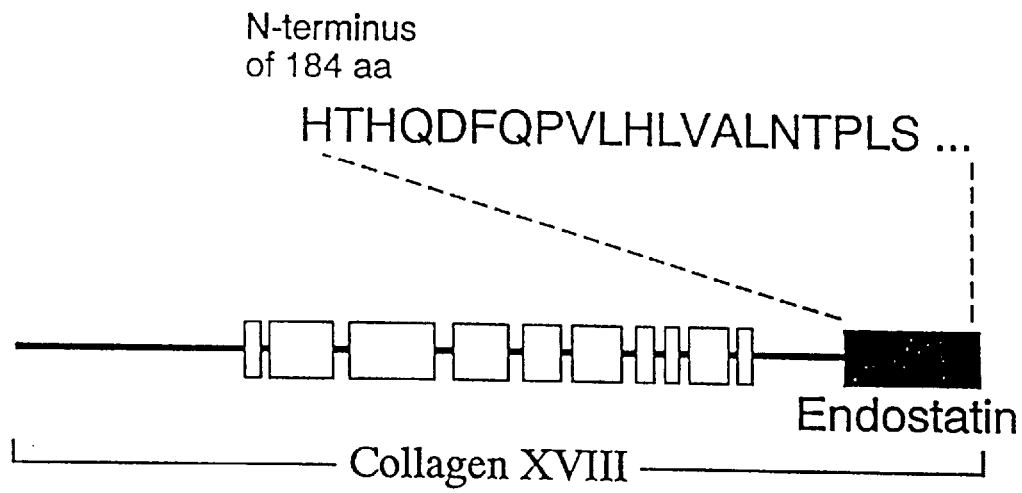

FIG. 5: N-terminal Amino Acid Sequence of An Inhibitor of Endothelial Cell Proliferation.

The N-terminal sequence of the purified inhibitor of endothelial cell proliferation is shown in relation to a schematic diagram of collagen type 18. The N-terminal sequence revealed identity of the inhibitor to an approximately 20 kDa C-terminal fragment (shown in solid shading) for collagen type XVIII. The open boxes represent the collagenase domains of collagen type XVIII.

Figure 6:
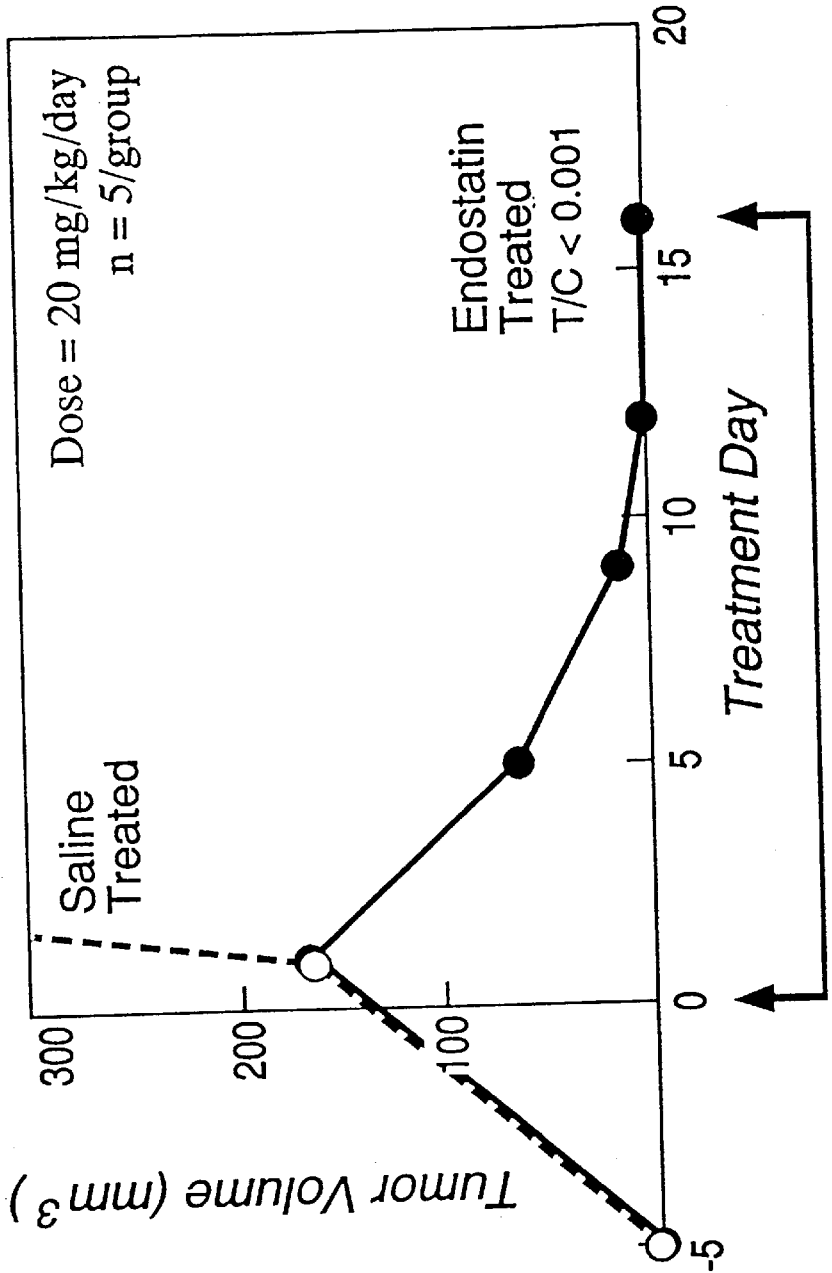

FIG. 6: Treatment of Lewis Lung Carcinoma With Recombinant Mouse Endostatin Inhibitor.

Recombinant inhibitor produced in $E.\ coli$ was administered to mice seeded with Lewis lung carcinoma that had achieved a tumor volume of approximately 150 mm$^3$. The inhibitor was administered at 20 mg/kg/day. Tumor mass regressed to non-detectable levels after approximately 12 days of treatment.

Figure 7A:
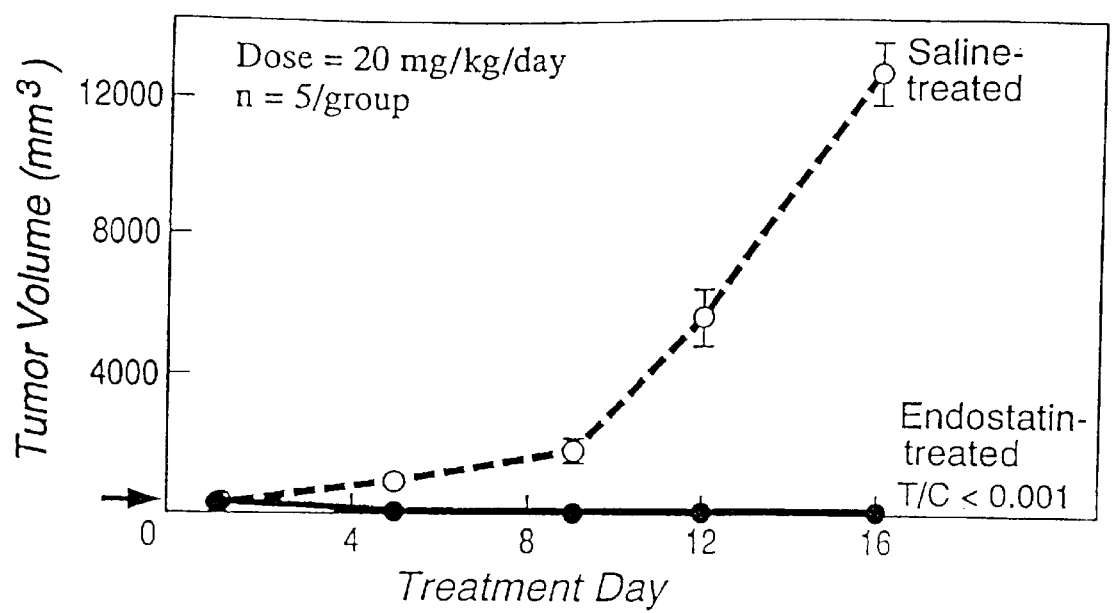
Figure 7B:
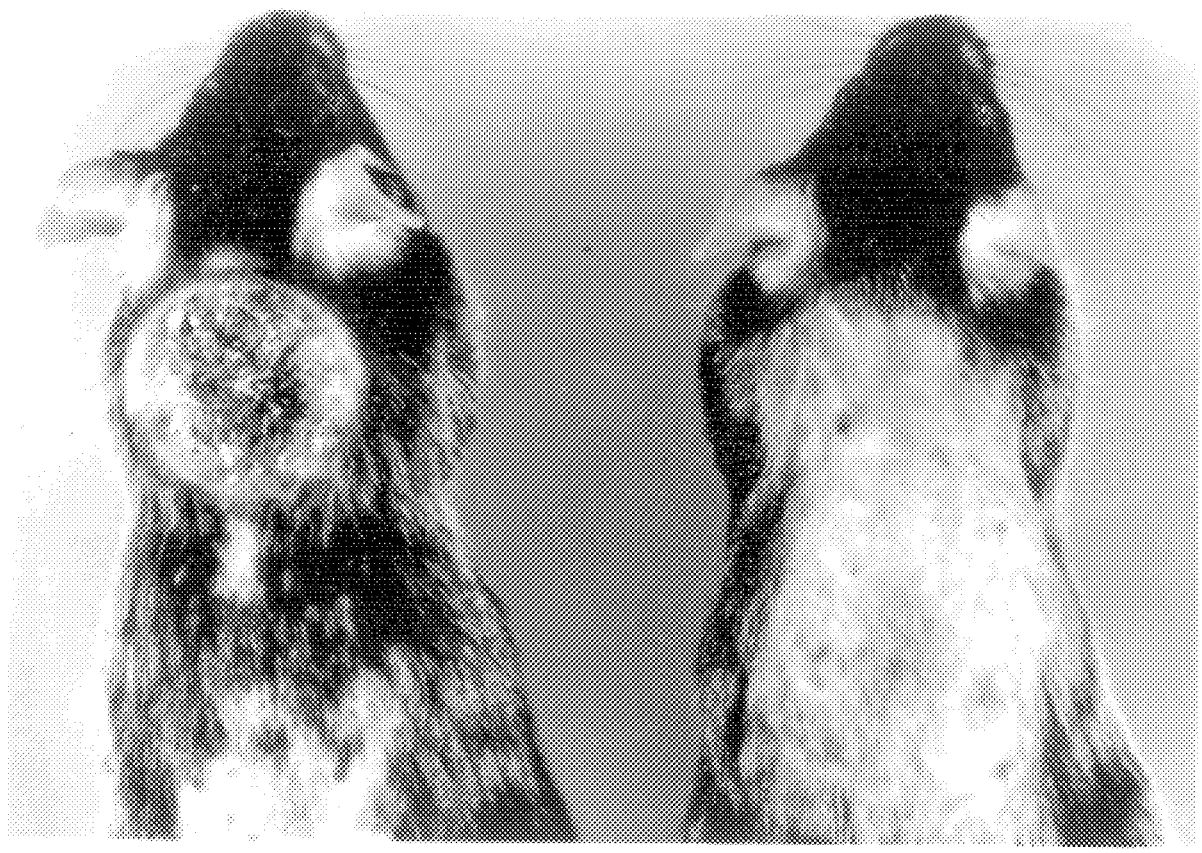
Figure 7C:
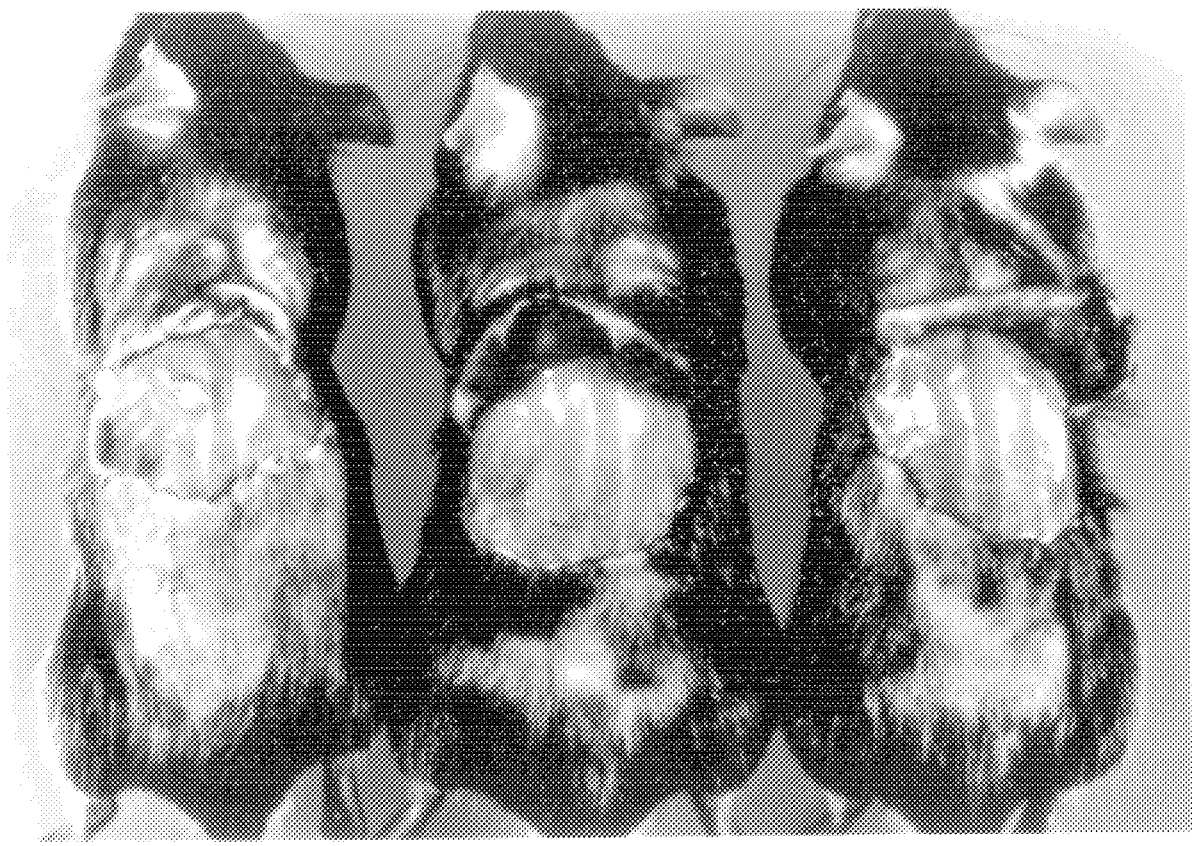

FIG. 7A–C: Systemic Therapy with Recombinant Endostatin Regresses Lewis Lung Carcinoma Primary Tumors.

FIG. 7A. Mice were implanted subcutaneously on the dorsum with Lewis lung carcinoma cells. Systemic therapy with recombinant mouse endostatin (20 mg/kg/day) was begun when tumors were approximately 200 mm$^3$ (1% of body weight). Tumors in the mice treated with endostatin inhibitor rapidly regressed and were inhibited by >99% relative to saline-treated controls. Each point represents mean ±SEM for 5 mice. The experiment was repeated with comparable results.

FIG. 7B. Representative treated and untreated tumor-bearing mice after 11 days of systemic therapy with endostatin. Saline-treated mice (right) had rapidly growing red tumors with ulcerated surfaces. Endostatin treated mice (left) had small pale residual tumors (arrow).

FIG. 7C. Residual disease in endostatin treated mice. Three of the five endostatin treated mice were sacrificed after 16 days of therapy. Autopsy revealed small white residual tumors at the site of the original primary implantation (arrows).

Figure 8:
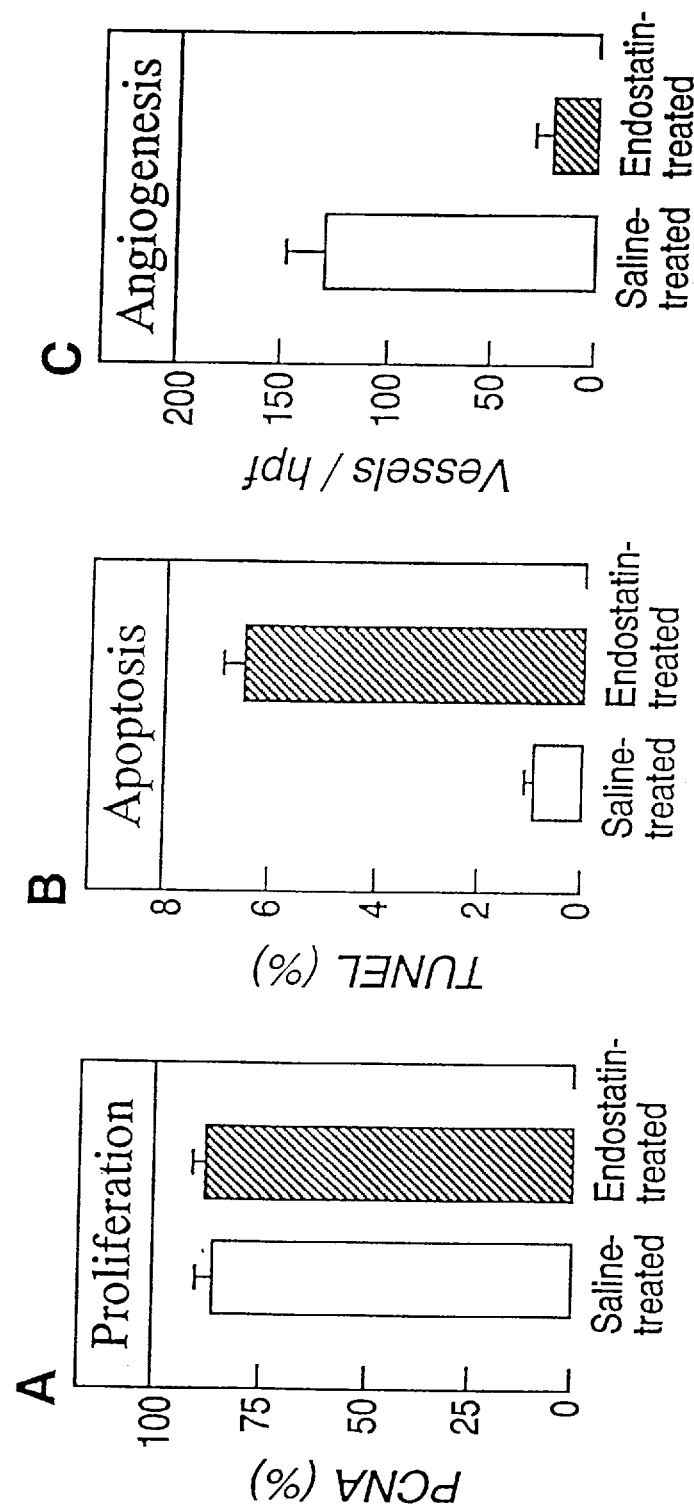

FIG. 8: Treatment of Murine T241 Fibrosarcoma with Recombinant Mouse Endostatinfrom $E.\ coli$.

Mice were seated with T241 Fibrosarcoma cells. Control mice were treated with saline. Experimental mice were treated with 20 mg/kg/day of recombinant mouse Endostatin directed from $E.\ coli$.

Figure 9:
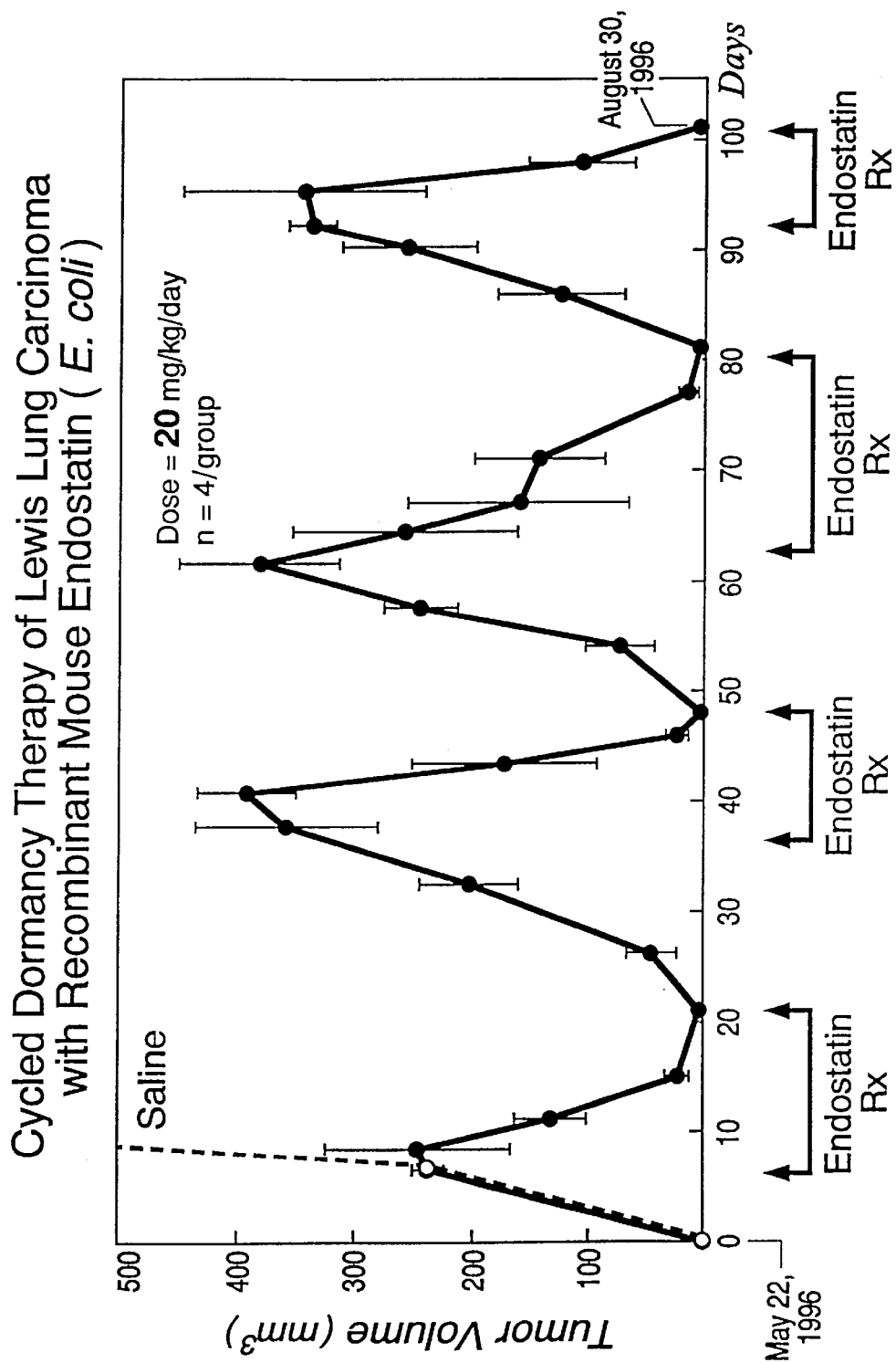

FIG. 9: Treatment of Murine B16F10 Melanoma with Recombinant Mouse Endostatin from $E.\ coli$.

Mice were seated with Murine B16F10 melanoma cells. Control animals were treated with saline. Experimental animals were treated with 20 mg/kg/day of recombinant mouse Endostatin direct from $E.\ coli$.

Figure 10:
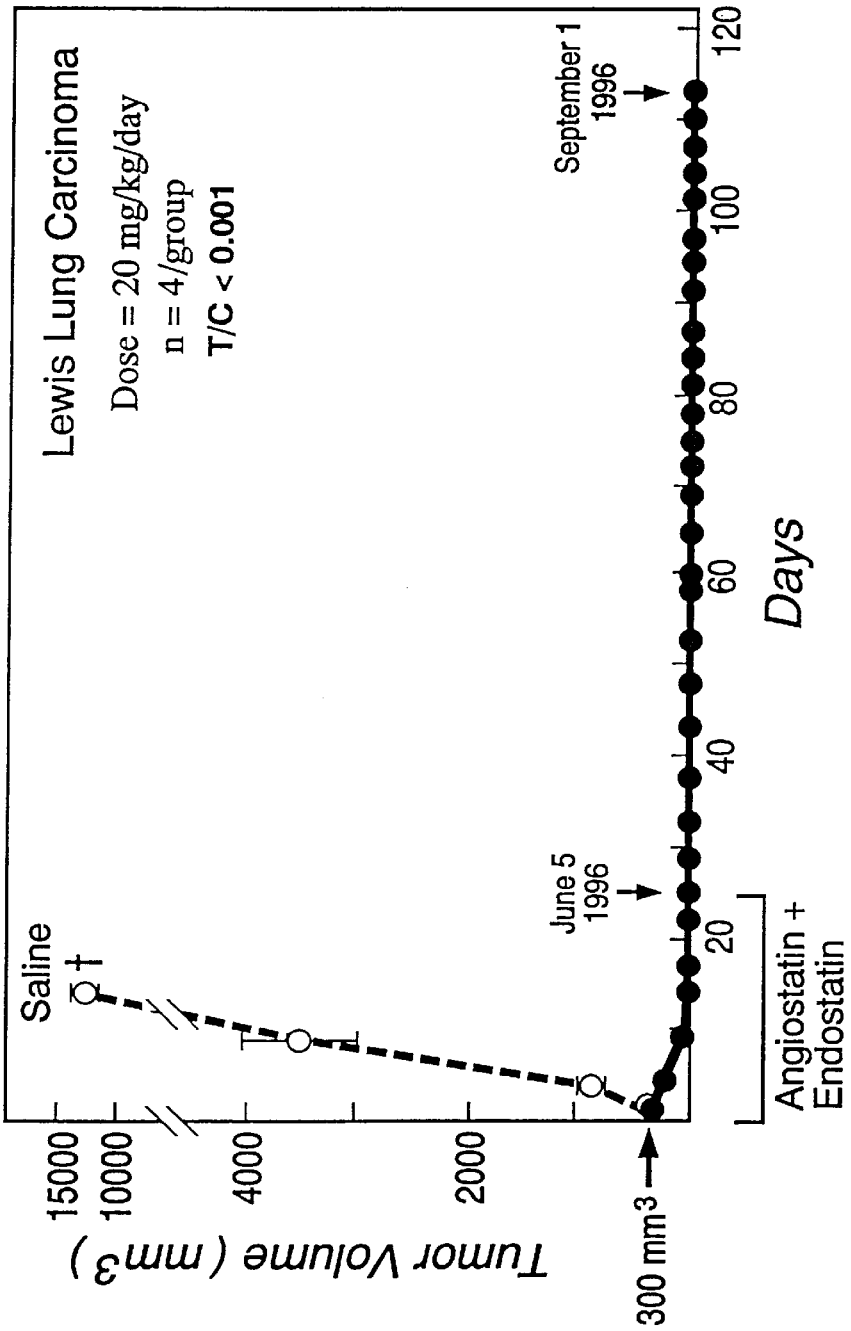

FIG. 10: Treatment of EOMA Hemangioendothelioma with Recombinant Mouse Endostatin from $E.\ coli$.

Mice were seated with EOMA hemangioendothelioma cells. Control animals were treated with saline. Experimental animals were treated with 20 mg/kg/day of Recombinant Mouse Endostatin direct from $E.\ coli$.

Figure 11:
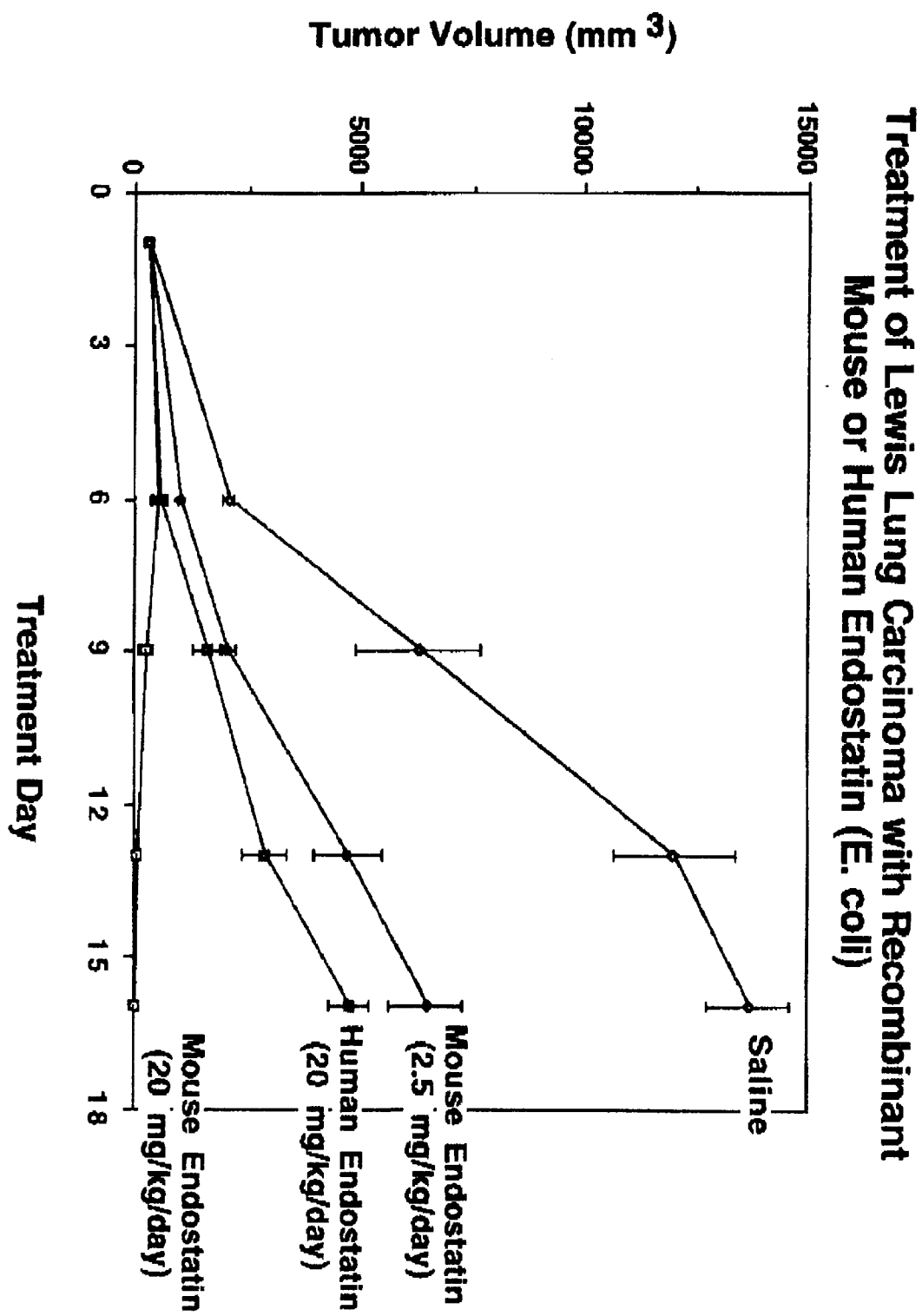

FIG. 11: Treatment of Lewis Lung Carcinoma with Recombinant Mouse or Human Endostatin direct from $E.\ coli$.

Mice were seated with Lewis Lung Carcinoma cells. Control animals were treated with saline. Experimental animals were treated with Recombinant Endostatin derived from the mouse sequence or Recombinant Endostatin direct from the human sequence, wherein both Endostatin are produced recombinantly in the $E.\ coli$. Mouse Endostatin was administered at either 20 mg/kg/day or 2.5 mg/kg/day, and Human Endostatin was administered at 20 mg/kg/day.

Figures 12A, 12B, 12C:
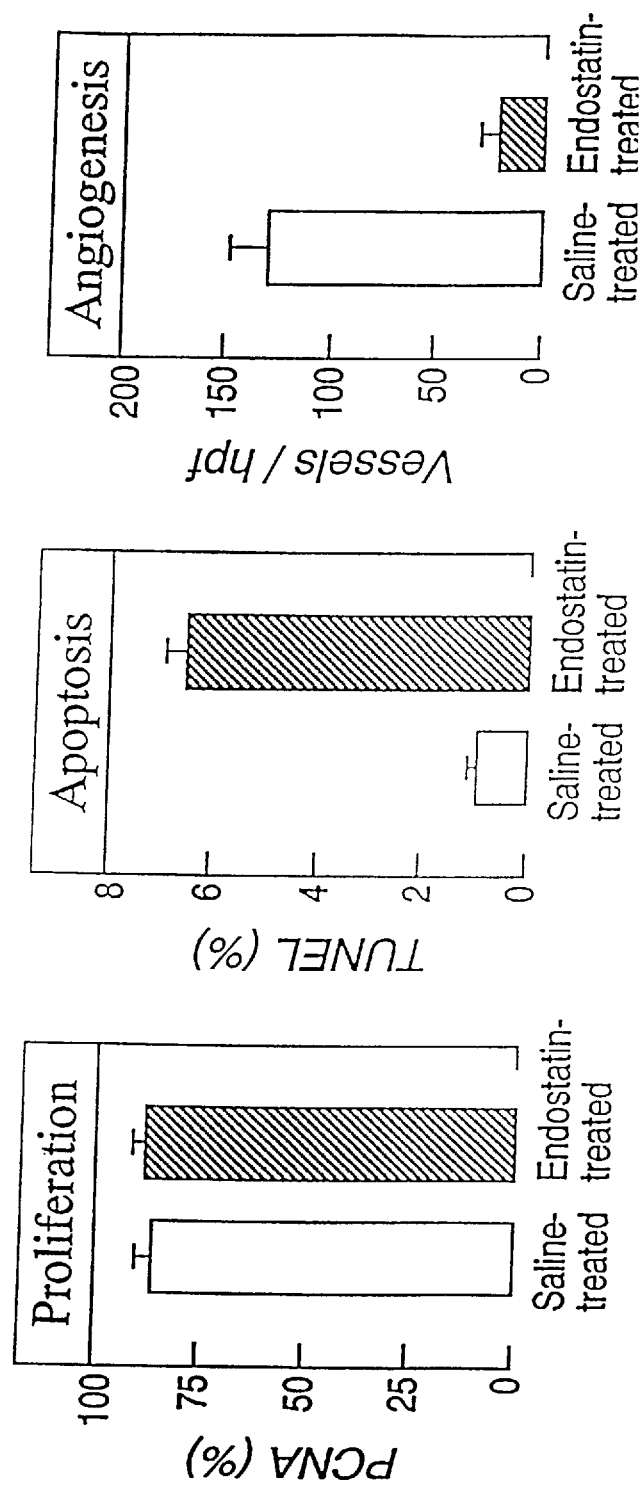

FIG. 12A–C: Endostatin Results in an Inhibition of Angiogenesis and an Increase in Apoptosis of Lewis Lung Carcinoma Primary Tumors.

Histological sections of tumors from saline versus endostatin treated mice implanted with Lewis lung carcinomas were analyzed for proliferation (PCNA), apoptosis (TUNEL), and angiogenesis (vWF). There was no significant difference in the proliferative index of tumor cells (FIG. 12A) in treated versus untreated tumors. In contrast, the apoptotic index of the tumor cells (FIG. 12B) increased 8-fold (p<0.001) in the endostatin treated mice. Vessel density (FIG. 12C) was determined by counting the number of capillary blood vessels per high-power field (HPF) in sections stained with antibodies against vWF. Angiogenesis was almost completely suppressed in the residual microscopic tumors of the endostatin treated mice (p<0.001).

Figure 13:
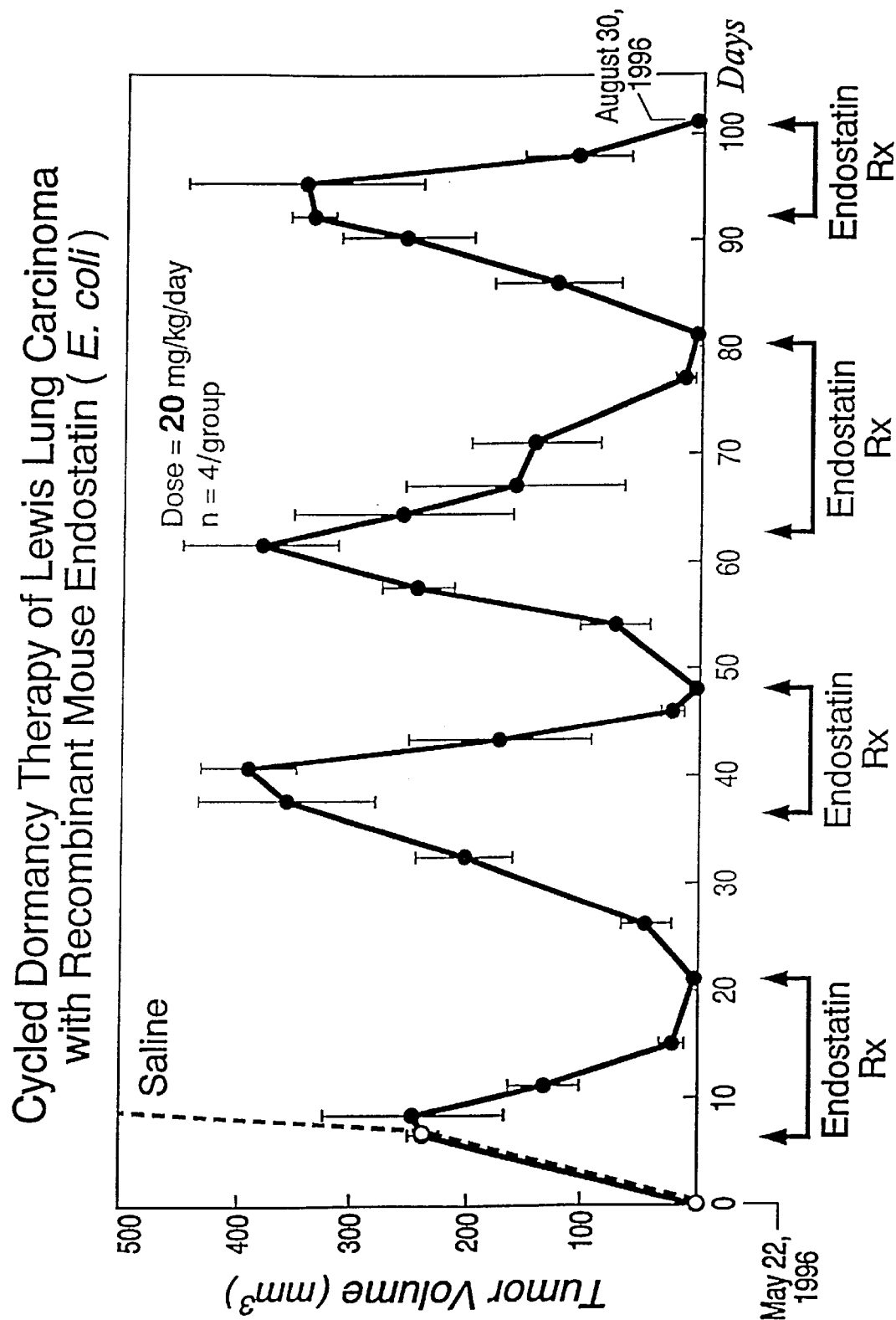

FIG. 13: Cycle Dormancy Therapy of Lewis Lung Carcinoma with Recombinant Mouse Endostatin From $E.\ Coli$.

Mice were implanted subcutaneously on the dorsum with Lewis lung carcinoma cells. Systemic therapy with recombinant mouse inhibitor (endostatin), administered at a dose of 20 mg/kg/day, was begun when tumors were approximately 200 mm$^3$ (1% of body weight). Tumors in the mice treated with the endostatin inhibitor rapidly regressed to essentially non-detectable levels after approximately 15 days of therapy. When treatment was terminated the tumor volume increased rapidly and was subsequently treatable to the same non-detectable levels by reinitiation of treatment. The peaks and valleys in the figure show the cycling effect of inhibition with endostatin.

Figure 14:
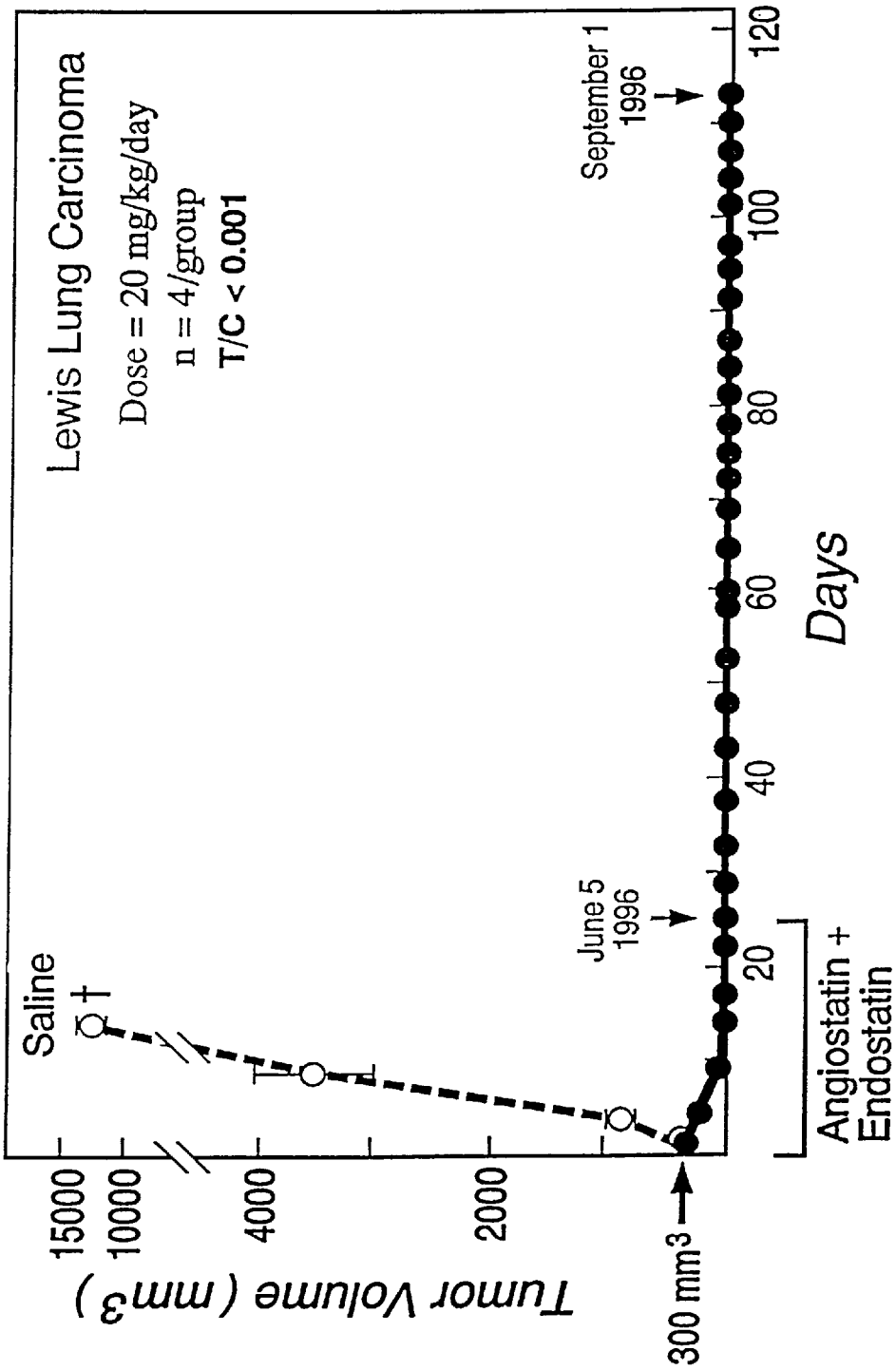

FIG. 14: Combination Therapy with Recombinant Mouse Angiostatin and Endostatin from $E.\ Coli$.

Mice were implanted subcutaneously on the dorsum with Lewis lung carcinoma cells. Systemic therapy with a combination of recombinant mouse endostatin (20 mg/kg/day) and recombinant mouse angiostatin (20 mg/kg/day) was begun when tumors were approximately 300 mm$^3$. Tumors in the mice treated with the combination therapy rapidly regressed to essentially non-detectable level in about 15 days. Importantly, the regressed tumors remained dormant and did not increase in size or mass after treatment was stopped. This is an unexpected result of substantial medical significance.

DETAILED DESCRIPTION OF THE INVENTION

Applicants have discovered a new class of protein molecules that have the ability to inhibit endothelial proliferation when added to proliferating endothelial cells in vitro. Accordingly, these protein molecules have been functionally defined as endostatins, however, it is to be understood that this functional definition is no way limits the bioactivity of endostatins to inhibition of endothelial cell growth in vitro or in vivo. Many other functions of endostatins are likely.

The term "endostatin" refers to a protein that is preferably 18 kDa to 20 kDa in size as determined by non-reduced and reduced gel electrophoresis, respectively. The term endostatin also includes precursor forms of the 18 kDa to 20 kDa protein. The term endostatin also includes fragments of the 18 kDa to 20 kDa protein and modified proteins and peptides that have a substantially similar amino acid sequence, and which are capable inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of the appended claims.

It will be appreciated that the term "endostatin" includes shortened proteins or peptides wherein one or more amino acid is removed from either or both ends of endostatin, or from an internal region of the protein, yet the resulting molecule retains endothelial proliferation inhibiting activity. The term "endostatin" also includes lengthened proteins or peptides wherein one or more amino acid is added to either or both ends of endostatin, or to an internal location in the protein, yet the resulting molecule retains endothelial proliferation inhibiting activity. Such molecules, for example with tyrosine added in the first position are useful for labeling such as radioiodination with $^{125}$iodine for use in assays. Labeling with other radioisotopes may be useful in providing a molecular tool for destroying the target cell containing endostatin receptors. Other labeling with molecules such as ricin may provide a mechanism for destroying cells with endostatin receptors.

"Substantial sequence homology" means at least approximately 70% homology between amino acid residue sequence in the endostatin analog sequence and that of endostatin, preferably at least approximately 80% homology, more preferably at least approximately 90% homology.

Also included in the definition of the term endostatin are modifications of the endostatin protein, its subunits and peptide fragments. Such modifications include substitutions of naturally occurring amino acids at specific sites with other molecules, including but not limited to naturally and non-naturally occurring amino acids. Such substitutions may modify the bioactivity of endostatin and produce biological or pharmacological agonists or antagonists. The term endostatin also includes an N terminal fragment of endostatin consisting of the sequence of the first 20N terminal amino acids which is shown in SEQ ID NO: 1 and is shown in Table 1. This sequence of the first 20N terminal amino acids corresponds to a C-terminal fragment of newly identified collagen type XVIII.

Table 1 shows the correspondence of 3 letter and 1 letter amino acid designations.

TABLE 1

| Amino Acid | Residue | Abbreviation |
|---|---|---|
| 1 | HIS | H |
| 2 | THR | T |
| 3 | HIS | H |
| 4 | GLN | Q |
| 5 | ASP | D |
| 6 | PHE | F |
| 7 | GLN | Q |
| 8 | PRO | P |
| 9 | VAL | V |
| 10 | LEU | L |
| 11 | HIS | H |
| 12 | LEU | L |
| 13 | VAL | V |
| 14 | ALA | A |

TABLE 1-continued

| Amino Acid | Residue | Abbreviation |
|---|---|---|
| 15 | LEU | L |
| 16 | ASN | N |
| 17 | THR | T |
| 18 | PRO | P |
| 19 | LEU | L |
| 20 | SER | S |

The N-terminal amino acid sequence of endostatin to an internal 20 amino acid peptide fragment found in collagen alpha 1 type XVIII starting at amino acid 1105 and amino acid 1124. The N-terminal amino acid sequence of the o corresponds to an internal 20 amino acid peptide fragment man collagen alpha 1 type XVIII starting at amino acid 1132 at amino acid 1151.

Endostatin can be isolated from murine hemangioendothelioma EOMA. Endostatin may be produced from recombinant sources, from genetically altered cells implanted into animals, from tumors, and from cell cultures as well as other sources. It is anticipated that endostatin is made in cells of the nervous system. Endostatin can be isolated from body fluids including, but not limited to, serum, urine and ascites, or synthesized by chemical or biological methods (e.g. cell culture, recombinant gene expression, peptide synthesis, and in vitro enzymatic catalysis of precursor molecules to yield active endostatin). Recombinant techniques include gene amplification from DNA sources using the polymerase chain reaction (PCR), and gene amplification from RNA sources using reverse transcriptase/PCR.

Endostatin specifically and reversibly inhibits endothelial cell proliferation. The inhibitor protein molecules of the invention are useful as a birth control drug, and for treating angiogenesis-related diseases, particularly angiogenesis-dependent cancers and tumors. The protein molecules are also useful for curing angiogenesis-dependent cancers and tumors. The unexpected and surprising ability of these novel compounds to treat and cure angiogenesis-dependent cancers and tumors answers a long felt unfulfilled need in the medical arts, and provides an important benefit to mankind.

Important terms that are used herein are defined as follows. "Cancer" means angiogenesis-dependent cancers and tumors, i.e. tumors that require for their growth (expansion in volume and/or mass) an increase in the number and density of the blood vessels supplying then with blood. "Regression" refers to the reduction of tumor mass and size.

The endothelial proliferation inhibiting proteins of the present invention can be made by automated protein synthesis methodologies well known to one skilled in the art. Alternatively, endothelial proliferation inhibiting proteins, or endostatins, of the present invention may be isolated from larger known proteins, such as human alpha 1 type XVIII collagen and mouse alpha 1 type XVIII collagen, proteins that share a common or similar N-terminal amino acid sequence. Examples of other potential endostatin source materials having similar N-terminal amino acid sequences include *Bos taurus* pregastric esterase, human alpha 1 type 15 collagen, NAD-dependent formate dehydrogenase (EC 1.2.1.2) derived from *Pseudomonas sp.*, s11459 hexon protein of bovine adenovirus type 3, CELF21D12 2 F21d12.3 *Caenorhabditis elegans* gene product, VAL1 TGMV AL1 protein derived from tomato golden mosaic virus, s01730 hexon protein derived from human adenovirus 12, *Saccharomyces cerevisiae*. For example, peptides closely related to endostatin may be derived from BOVMPE 1 pregastric esterase (BOS TAURUS) gene sequence corresponding to amino acids 502 to 521, and collagen alpha 1 type 15 from humans beginning at amino acid 316 ending at 335.

Proteins and peptides derived from these and other sources, including manual or automated protein synthesis, may be quickly and easily tested for endothelial proliferation inhibiting activity using a biological activity assay such as the bovine capillary endothelial cell proliferation assay. Other bioassays for inhibiting activity include the chick CAM assay, the mouse corneal assay, and the effect of administering isolated or synthesized proteins on implanted tumors. The chick CAM assay is described by O'Reilly, et al. in "Angiogenic Regulation of Metastatic Growth" *Cell*, vol. 79 (2), Oct. 21, 1994, pp. 315–328, which is hereby incorporated by reference in its entirety. Briefly, 3 day old chicken embryos with intact yolks are separated from the egg and placed in a petri dish. After 3 days of incubation a methylcellulose disc containing the protein to be tested is applied to the CAM of individual embryos. After 48 hours of incubation, the embryos and CAMs are observed to determine whether endothelial growth has been inhibited. The mouse corneal assay involves implanting a growth factor-containing pellet, along with another pellet containing the suspected endothelial growth inhibitor, in the cornea of a mouse and observing the pattern of capillaries that are elaborated in the cornea.

Applicants' invention also encompasses nucleic acid sequences that correspond to and code for the endothelial proliferation-inhibiting protein molecules of the invention, and to monoclonal and polyclonal antibodies that bind specifically to such protein molecules. The biologically active protein molecules, nucleic acid sequences corresponding to the proteins, and antibodies that bind specifically to the proteins of the present invention are useful for modulating endothelial processes in vivo, and for diagnosing and treating endothelial cell-related diseases, for example by gene therapy.

Nucleic acid sequences that correspond to, and code for, endostatin and endostatin analogs can be prepared based upon the knowledge of the amino acid sequence, and the art recognized correspondence between codons (sequences of three nucleic acid bases), and amino acids. Because of the degeneracy of the genetic code, wherein the third base in a codon may vary yet still code for the same amino acid, many different possible coding nucleic acid sequences are derivable for any particular protein or peptide fragment.

Nucleic acid sequences are synthesized using automated systems well known in the art. Either the entire sequence may be synthesized or a series of smaller oligonucleotides are made and subsequently ligated together to yield the full length sequence. Alternatively, the nucleic acid sequence may be derived from a gene bank using oligonucleotides probes designed based on the N-terminal amino acid sequence and well known techniques for cloning genetic material.

The present invention also includes the detection of endostatin in body fluids and tissues for the purpose of diagnosis or prognosis of angiogenesis-mediated diseases such as cancer. The present invention also includes the detection of endostatin binding sites and receptors in cells and tissues. The present invention also includes methods of treating or preventing angiogenic diseases and processes including, but not limited to, arthritis and tumors by stimulating the production of endostatin, and/or by administering substantially purified endostatin, or endostatin agonists or antagonists, and/or endostatin antisera or antisera directed against endostatin antisera to a patient. Additional treatment methods include administration of endostatin, endostatin fragments, endostatin antisera, or endostatin receptor agonists and antagonists linked to cytotoxic agents. It is to be understood that the endostatin can be animal or human in origin. Endostatin can also be produced synthetically by chemical reaction or by recombinant techniques in conjunction with expression systems. Endostatin can also be produced by enzymatically cleaving different molecules, including endostatin precursors, containing sequence homology or identity with segments of endostatin to generate peptides having anti-angiogenesis activity.

Passive antibody therapy using antibodies that specifically bind endostatin can be employed to modulate endothelial-dependent processes such as reproduction, development, and wound healing and tissue repair. In addition, antisera directed to the Fab regions of endostatin antibodies can be administered to block the ability of endogenous endostatin antisera to bind endostatin.

Antibodies specific for endostatin and endostatin analogs are made according to techniques and protocols well known in the art. The antibodies may be either polyclonal or monoclonal. The antibodies are utilized in well know immunoassay formats, such as competitive and non-competitive immunoassays, including ELISA, sandwich immunoassays and radioimmunoassays (RIAs), to determine the presence or absence of the endothelial proliferation inhibitors of the present invention in body fluids. Examples of body fluids include but are not limited to blood, serum, peritoneal fluid, pleural fluid, cerebrospinal fluid, uterine fluid, saliva, and mucus.

The proteins, nucleic acid sequences and antibodies of the present invention are useful for diagnosing and treating endothelial cell-related diseases and disorders. A particularly important endothelial cell process is angiogenesis, the formation of blood vessels. Angiogenesis-related diseases may be diagnosed and treated using the endothelial cell proliferation inhibiting proteins of the present invention. Angiogenesis-related diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. The endothelial cell proliferation inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helobacter pylori*).

The endothelial cell proliferation inhibiting proteins can be used as a birth control agent by reducing or preventing uterine vascularization required for embryo implantation. Thus, the present invention provides an effective birth control method when an amount of the inhibitory protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possible a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that endostatin administration will interfere with normal enhanced vascularization of the placenta, and also with the development of vessels within a successfully implanted blastocyst and developing embryo and fetus.

Conversely, blockade of endostatin receptors with endostatin analogs which act as receptor antagonists may promote endothelialization and vascularization. Such effects may be desirable in situations of inadequate vascularization of the uterine endometrium and associated infertilty, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

A surprising discovery is that un-refolded and non-soluble recombinant endostatin is also a potent anti-angiogenesis compound which serves as a sustained release depot when administered to a patient.

The present invention also relates to methods of using endostatin and endothelial cell proliferation inhibiting peptide fragments of endostatin, nucleic acid sequences corresponding to endostatin and active peptide fragments thereof, and antibodies that bind specifically to endostatin and its peptides, to diagnose endothelial cell-related diseases and disorders.

The invention further encompasses a method for identifying endostatin-specific receptors, and the receptor molecules identified and isolated thereby.

The present invention also provides a method for quantitation of endostatin receptors.

A particularly important aspect of the present invention is the discovery of a novel and effective method for treating and curing angiogenesis-dependent cancer in patients. It was unexpectedly found that the co-administration of endostatin and angiostatin in an amount sufficient to inhibit tumor growth and cause sustainable regression of tumor mass to microscopic size cures angiogenesis-dependent cancer. Accordingly, the present invention also includes formulations effective for treating or curing angiogenesis-dependent cancers and tumors.

More particularly, recombinant mouse endostatin, from insect cells or E. coli, potently inhibits angiogenesis and the growth of metastases and primary tumors. In a novel method of sustained release, the E. coli-derived recombinant endostatin was administered as an un-refolded suspension in an amount sufficient to inhibit angiogenesis, thereby inhibiting tumor growth. Tumor mass was reduced when recombinant endostatin was administered in an amount sufficient to cause regression of the tumor. Primary tumors of 1–2% of body weight regressed by greater than 150-fold to become microscopic dormant lesions when treated by endostatin. Immunohistochemical analysis of the dormant tumors revealed blocked angiogenesis accompanied by high proliferation of the tumor cells balanced by a high rate of tumor cell apoptosis. There was no evidence of toxicity in any of the mice treated with endostatin.

It is contemplated as part of the present invention that endostatin can be isolated from a body fluid such as blood or urine of patients or the endostatin can be produced by recombinant DNA methods or synthetic peptide chemical methods that are well known to those of ordinary skill in the art. Protein purification methods are well known in the art and a specific example of a method for purifying endostatin, and assaying for inhibitor activity is provided in the examples below. Isolation of human endogenous endostatin is accomplished using similar techniques.

One example of a method of producing endostatin using recombinant DNA techniques entails the steps of (1) identifying and purifying an endostatin as discussed above, and as more fully described below, (2) determining the N-terminal amino acid sequence of the purified inhibitor, (3) synthetically generating a DNA oligonucleotide probe that corresponds to the N-terminal amino acid sequence, (4) generating a DNA gene bank from human or other mammalian DNA, (5) probing the gene bank with the DNA oligonucleotide probe, (6) selecting clones that hybridize to the oligonucleotide, (7) isolating the inhibitor gene from the clone, (8) inserting the gene into an appropriate vector such as an expression vector, (9) inserting the gene-containing vector into a microorganism or other expression system capable of expressing the inhibitor gene, and (10) isolating the recombinantly produced inhibitor. The above techniques are more fully described in laboratory manuals such as "Molecular Cloning: A Laboratory Manual" Second Edition by Sambrook et al., Cold Spring Harbor Press, 1989.

The gene for endostatin may also be isolated from cells or tissue (such as tumor cells) that express high levels of endostatin by (1) isolating messenger RNA from the tissue, (2) using reverse transcriptase to generate the corresponding DNA sequence and then (3) using PCR with the appropriate primers to amplify the DNA sequence coding for the active endostatin amino acid sequence.

Yet another method of producing endostatin, or biologically active fragments thereof, is by peptide synthesis. Once a biologically active fragment of an endostatin is found using the assay system described more fully below, it can be sequenced, for example by automated peptide sequencing methods. Alternatively, once the gene or DNA sequence which codes for endostatin is isolated, for example by the methods described above, the DNA sequence can be determined, which in turn provides information regarding the amino acid sequence. Thus, if the biologically active fragment is generated by specific methods, such as tryptic digests, or if the fragment is N-terminal sequenced, the remaining amino acid sequence can be determined from the corresponding DNA sequence.

Once the amino acid sequence of the peptide is known, for example the N-terminal 20 amino acids, the fragment can be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for agonistic and antagonistic activity in vitro and in vivo. Peptide fragments that possess high affinity binding to tissues can be used to isolate the endostatin receptor on affinity columns. Isolation and purification of the endostatin receptor is a fundamental step towards elucidating the mechanism of action of endostatin. This facilitates development of drugs to modulate the activity of the endostatin receptor, the final pathway to biological activity. Isolation of the receptor enables the construction of nucleotide probes to monitor the location and synthesis of the receptor, using in situ and solution hybridization technology.

Endostatin is effective in treating diseases or processes that are mediated by, or involve, angiogenesis. The present invention includes the method of treating an angiogenesis mediated disease with an effective amount of endostatin or endostatin agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation. Endostatin is useful in the treatment of disease of excessive or abnormal stimulation of endothelial cells. These diseases include, but are not limited to, intestinal adhesions, atherosclerosis, scleroderma, and hypertrophic scars, i.e., keloids. Endostatin can be used as a birth control agent by preventing vascularization required for blastocyst implantation and for development of the placenta, the blastcyst, the embryo and the fetus.

The synthetic peptide fragments of endostatin have a variety of uses. The peptide that binds to the endostatin receptor with high specificity and avidity is radiolabeled and employed for visualization and quantitation of binding sites using autoradiographic and membrane binding techniques. This application provides important diagnostic and research tools. Knowledge of the binding properties of the endostatin receptor facilitates investigation of the transduction mechanisms linked to the receptor.

In addition, labeling these peptides with short lived isotopes enables visualization of receptor binding sites in vivo using positron emission tomography or other modern radiographic techniques in order to locate tumors with endostatin binding sites.

Systematic substitution of amino acids within these synthesized peptides yields high affinity peptide agonists and antagonists to the endostatin receptor that enhance or diminish endostatin binding to its receptor. Such agonists are used to suppress the growth of micrometastases, thereby limiting the spread of cancer. Antagonists to endostatin are applied in situations of inadequate vascularization, to block the inhibitory effects of angiostatin and possibly promote angiogenesis. This treatment may have therapeutic effects to promote wound healing in diabetics.

Endostatin peptides are employed to develop affinity columns for isolation of the endostatin receptor from cultured tumor cells. Isolation and purification of the endostatin receptor is followed by amino acid sequencing. Next, nucleotide probes are developed for insertion into vectors for expression of the receptor. These techniques are well known to those skilled in the art. Transfection of the endostatin receptor into tumor cells enhances the responsiveness of these cells to endogenous or exogenous endostatin and thereby decreasing the rate of metastatic growth.

Cytotoxic agents, such as ricin, are linked to endostatin, and high affinity endostatin peptide fragments, thereby providing a tool for destruction of cells that bind endostatin. These cells may be found in many locations, including but not limited to, micrometastases and primary tumors. Peptides linked to cytotoxic agents are infused in a manner designed to maximize delivery to the desired location. For example, ricin-linked high affinity endostatin fragments are delivered through a cannula into vessels supplying the target site or directly into the target. Such agents are also delivered in a controlled manner through osmotic pumps coupled to infusion cannulae. A combination of endostatin antagonists may be co-applied with stimulators of angiogenesis to increase vascularization of tissue. This therapeutic regimen provides an effective means of destroying metastatic cancer.

According to the present invention, endostatin may be used in combination with other compositions and procedures for the treatment of diseases. For example, a tumor may be treated conventionally with surgery, radiation or chemotherapy combined with endostatin and then endostatin may be subsequently administered to the patient to extend the dormancy of micrometastases and to stabilize any residual primary tumor.

The endostatin of the present invention also can be used to generate antibodies that are specific for the inhibitor. The antibodies can be either polyclonal antibodies or monoclonal antibodies. These antibodies that specifically bind to the endostatin can be used in diagnostic methods and kits that are well known to those of ordinary skill in the art to detect or quantify the endostatin in a body fluid or tissue. Results from these tests can be used to diagnose or predict the occurrence or recurrence of a cancer and other angiogenesis mediated diseases.

The endostatin also can be used in a diagnostic method and kit to detect and quantify antibodies capable of binding endostatin. These kits would permit detection of circulating endostatin antibodies which indicates the spread of micrometastases in the presence of endostatin secreted by primary tumors in situ. Patients that have such circulating anti- endostatin antibodies may be more likely to develop tumors and cancers, and may be more likely to have recurrences of cancer after treatments or periods of remission. The Fab fragments of these anti- endostatin antibodies may be used as antigens to generate anti- endostatin Fab-fragment antisera which can be used to neutralize the removal of circulating endostatin by anti- endostatin antibodies.

Another aspect of the present invention is a method of blocking the action of excess endogenous endostatin. This can be done by passively immunizing a human or animal with antibodies specific for the undesired endostatin in the system. This treatment can be important in treating abnormal ovulation, menstruation and placentation, and vasculogenesis. This provides a useful tool to examine the effects of endostatin removal on metastatic processes. The Fab fragment of endostatin antibodies contains the binding site for endostatin. This fragment is isolated from endostatin antibodies using techniques known to those skilled in the art. The Fab fragments of endostatin antisera are used as antigens to generate production of anti-Fab fragment serum. Infusion of this antiserum against the Fab fragments of endostatin prevents endostatin from binding to endostatin antibodies. Therapeutic benefit is obtained by neutralizing endogenous anti- endostatin antibodies by blocking the binding of endostatin to the Fab fragments of anti- endostatin. The net effect of this treatment is to facilitate the ability of endogenous circulating endostatin to reach target cells, thereby decreasing the spread of metastases.

It is to be understood that the present invention is contemplated to include any derivatives of the endostatin that have endothelial inhibitory activity. The present invention includes the entire endostatin protein, derivatives of the endostatin protein and biologically-active fragments of the endostatin protein. These include proteins with endostatin activity that have amino acid substitutions or have sugars or other molecules attached to amino acid functional groups. The present invention also includes genes that code for endostatin and the endostatin receptor, and to proteins that are expressed by those genes.

The proteins and protein fragments with the endostatin activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the endostatin may be incorporated into biodegradable polymers allowing for sustained release of the compound, the polymers being implanted in the vicinity of where drug delivery is desired, for example, at the site of a tumor or implanted so that the endostatin is slowly released systemically. Osmotic minipumps may also be used to provide controlled delivery of high concentrations of endostatin through cannulae to the site of interest, such as directly into a metastatic growth or into the vascular supply to that tumor. The biodegradable polymers and their use are described, for example, in detail in Brem et al., *J. Neurosurg.* 74:441–446 (1991), which is hereby incorporated by reference in its entirety.

The dosage of the endostatin of the present invention will depend on the disease state or condition being treated and other clinical factors such as weight and condition of the human or animal and the route of administration of the compound. For treating humans or animals, between approximately 0.5 mg/kilogram to 500 mg/kilogram of the endostatin can be administered. A more preferable range is 1 mg/kilogram to 100 mg/kilogram with the most preferable range being from 2 mg/kilogram to 50 mg/kilogram. Depending upon the half-life of the endostatin in the particular animal or human, the endostatin can be administered between several times per day to once a week. It is to be understood that the present invention has application for both human and veterinary use. The methods of the present invention contemplate single as well as multiple administrations, given either simultaneously or over an extended period of time.

The endostatin formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The endostatin formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations of the present invention may include other agents conventional in the art having regard to the type of formulation in question.

Different peptide fragments of the intact endostatin molecule can be synthesized for use in several applications including, but not limited to the following; as antigens for the development of specific antisera, as agonists and antagonists active at endostatin binding sites, as peptides to be linked to cytotoxic agents for targeted killing of cells that bind endostatin. The amino acid sequences that comprise these peptides are selected on the basis of their position on the exterior regions of the molecule and are accessible for binding to antisera. The amino and carboxyl termini of endostatin, as well as the mid-region of the molecule are represented separately among the fragments to be synthesized. The amino terminus distal to the 20th amino acid and carboxyl termini of endostatin may contain or be modified to contain tyrosine and lysine residues and are labeled with many techniques. A tyrosine or lysine is added to fragments that do not have these residues to facilitate labeling of reactive amino and hydroxyl groups on the peptide. These peptide sequences are compared to known sequences using sequence data banks to determine potential sequence homologies. This information facilitates elimination of sequences that exhibit a high degree of sequence homology to other molecules, thereby enhancing the potential for high specificity in the development of antisera, agonists and antagonists to endostatin.

Peptides can be synthesized in a standard microchemical facility and purity checked with HPLC and mass spectrophotometry. Methods of peptide synthesis, HPLC purification and mass spectrophotometry are commonly known to those skilled in these arts.

Peptides and endostatin are also produced in recombinant *E. coli*, as described below, or in insect or yeast expression systems, and purified with column chromatography.

Endostatin and endostatin derived peptides can be coupled to other molecules using standard methods. The amino terminus distal to the 20th amino acid and the carboxyl terminus of endostatin may both contain tyrosine and lysine residues and are isotopically and nonisotopically labeled with many techniques, for example radiolabeling using conventional techniques (tyrosine residues- chloramine T, iodogen, lactoperoxidase; lysine residues- Bolton-Hunter reagent). These coupling techniques are well known to those skilled in the art. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Endostatin peptides are chemically coupled to isotopes, enzymes, carrier proteins, cytotoxic agents, fluorescent molecules and other compounds for a variety of applications. The efficiency of the coupling reaction is determined using different techniques appropriate for the specific reaction. For example, radiolabeling of an endostatin peptide or protein with $^{125}$I is accomplished using chloramine T and Na$^{125}$I of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted Na$^{125}$I is separated from the labeled endostatin peptide. The peptide fractions with the highest specific radioactivity are stored for subsequent use such as analysis of the ability to bind to endostatin antisera.

Another application of peptide conjugation is for production of polyclonal antisera. For example, endostatin peptides containing lysine residues are linked to purified bovine serum albumin using glutaraldehyde. The efficiency of the reaction is determined by measuring the incorporation of radiolabeled peptide. Unreacted glutaraldehyde and peptide are separated by dialysis. The conjugate is stored for subsequent use.

Antiserum against endostatin can be generated. After peptide synthesis and purification, both monoclonal and polyclonal antisera are raised using established techniques known to those skilled in the art. For example, polyclonal antisera may be raised in rabbits, sheep, goats or other animals. Endostatin peptides conjugated to a carrier molecule such as bovine serum albumin, or endostatin itself, is combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4° C. and are centrifuged at approximately 2400×g at 4° C. for about 30 minutes. The serum is removed, aliquoted, and stored at 4° C. for immediate use or at −20° to −90° C. for subsequent analysis.

All serum samples from generation of polyclonal antisera or media samples from production of monoclonal antisera are analyzed for determination of titer. Titer is established through several means, for example, using dot blots and density analysis, and also with precipitation of radiolabeled peptide-antibody complexes using protein A, secondary antisera, cold ethanol or charcoal-dextran followed by activity measurement with a gamma counter. The highest titer antisera are also purified on affinity columns which are commercially available. Endostatin peptides are coupled to the gel in the affinity column. Antiserum samples are passed through the column and anti- endostatin antibodies remain bound to the column. These antibodies are subsequently eluted, collected and evaluated for determination of titer and specificity.

The highest titer endostatin antisera is tested to establish the following; a) optimal antiserum dilution for highest specific binding of the antigen and lowest non-specific binding, b) the ability to bind increasing amounts of endostatin peptide in a standard displacement curve, c) potential cross-reactivity with related peptides and proteins, including endostatin related species, d) ability to detect endostatin peptides in extracts of plasma, urine, tissues, and in cell culture media.

Kits for measurement of endostatin are also contemplated as part of the present invention. Antisera that possess the highest titer and specificity and can detect endostatin peptides in extracts of plasma, urine, tissues, and in cell culture media are further examined to establish easy to use kits for rapid, reliable, sensitive, and specific measurement and localization of angiostatin. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and inter-assay variation is established at 20%, 50% and 80% points on the standard curves of displacement or activity.

One example of an assay kit commonly used in research and in the clinic is a radioimmunoassay (RIA) kit. An endostatin RIA is illustrated below. After successful radio-iodination and purification of endostatin or an endostatin peptide, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4° C. for 24 hours, protein A is added and the tubes are vortexed, incubated at room temperature for 90 minutes, and centrifuged at approximately 2000–2500×g at 4° C. to precipitate the complexes of antibody bound to labeled antigen. The supernatant is removed by aspiration and the radioactivity in the pellets counted in a gamma counter. The antiserum dilution that binds approximately 10 to 40% of the labeled peptide after subtraction of the non-specific binding is further characterized.

Next, a dilution range (approximately 0.1 pg to 10 ng) of the endostatin peptide used for development of the antiserum is evaluated by adding known amounts of the peptide to tubes containing radiolabeled peptide and antiserum. After an additional incubation period, for example, 24 to 48 hours, protein A is added and the tubes centrifuged, supernatant removed and the radioactivity in the pellet counted. The displacement of the binding of radiolabeled endostatin peptide by the unlabeled endostatin peptide (standard) provides a standard curve. Several concentrations of other endostatin peptide fragments, plasminogen, endostatin from different species, and homologous peptides are added to the assay tubes to characterize the specificity of the endostatin antiserum.

Extracts of various tissues, including but not limited to, primary and secondary tumors, Lewis lung carcinoma, cultures of endostatin producing cells, placenta, uterus, and other tissues such as brain, liver, and intestine, are prepared using extraction techniques that have been successfully employed to extract endostatin. After lyophilization or Speed Vac of the tissue extracts, assay buffer is added and different aliquots are placed into the RIA tubes. Extracts of known endostatin producing cells produce displacement curves that are parallel to the standard curve, whereas extracts of tissues that do not produce endostatin do not displace radiolabeled endostatin from the endostatin antiserum. In addition, extracts of urine, plasma, and cerebrospinal fluid from animals with Lewis lung carcinoma are added to the assay tubes in increasing amounts. Parallel displacement curves indicate the utility of the endostatin assay to measure endostatin in tissues and body fluids.

Tissue extracts that contain endostatin are additionally characterized by subjecting aliquots to reverse phase HPLC. Eluate fractions are collected, dried in Speed Vac, reconstituted in RIA buffer and analyzed in the endostatin RIA. The maximal amount of endostatin immunoreactivity is located in the fractions corresponding to the elution position of endostatin.

The assay kit provides instructions, antiserum, endostatin or endostatin peptide, and possibly radiolabeled endostatin and/or reagents for precipitation of bound endostatin—endostatin antibody complexes. The kit is useful for the measurement of endostatin in biological fluids and tissue extracts of animals and humans with and without tumors.

Another kit is used for localization of angiostatin in tissues and cells. This endostatin immunohistochemistry kit provides instructions, endostatin antiserum, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This endostatin immunohistochemistry kit permits localization of endostatin in tissue sections and cultured cells using both light and electron microscopy. It is used for both research and clinical purposes. For example, tumors are biopsied or collected and tissue sections cut with a microtome to examine sites of endostatin production. Such information is useful for diagnostic and possibly therapeutic purposes in the detection and treatment of cancer.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1
Identification of an Inhibitor of Capillary Endothelial Cell Proliferation from Hemangioendothelioma Cells A murine hemangioendothelioma cell line, EOMA (Obeso et al., 1990), was evaluated for evidence of the production of inhibitors of endothelial cell proliferation. Many of the known endogenous inhibitors of angiogenesis inhibit the in vitro proliferation of endothelial cells.

Figure 1:
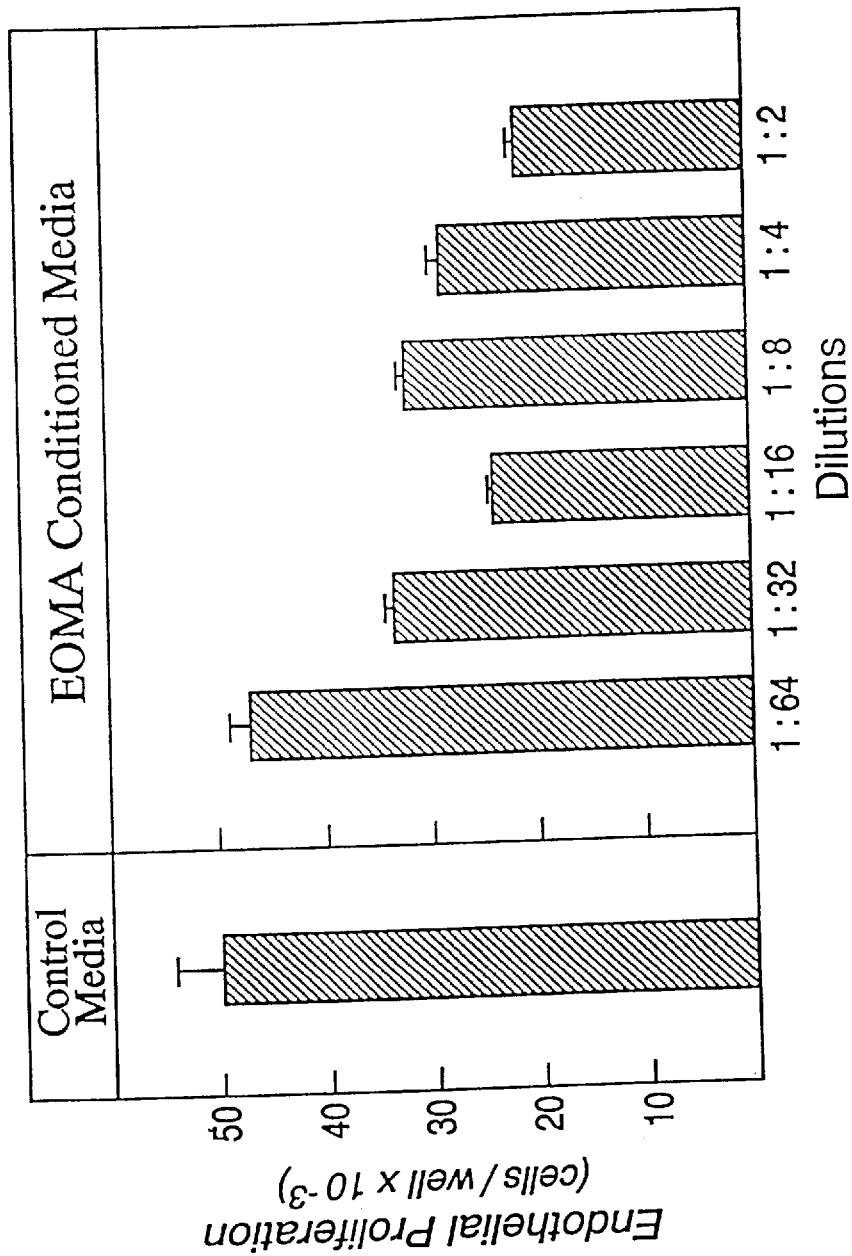
FIG. 1: Inhibition of Capillary Endothelial Cell Proliferation by Conditioned Media from EOMA Cells.

Conditioned Media Collection: Cells of the murine hemangioendothelioma cell line EOMA were maintained in DMEM supplemented with 10% bovine calf serum (BCS) and 1% glutamine-penicillin-streptomycin (GPS) in a 37° C. and 10% $CO_2$ incubator. Conditioned media from EOMA cells (i.e. culture media used to grow EOMA cells) was applied to bovine capillary endothelial cells, stimulated with bFGF, in a 72 hour proliferation assay. The conditioned media reversibly inhibited the proliferation of capillary endothelial cells as compared to controls. The pattern of inhibition was consistent with the presence of inhibitory and stimulatory activity of endothelial cell proliferation (FIG. 1).

EXAMPLE 2
Inhibitory Activity of Endothelial Cell Proliferation is not due to Angiostatin To determine if the inhibitor of capillary endothelial cell proliferation produced by the EOMA cells was angiostatin, pooled conditioned media was applied to a lysine column (lysine conjugated to Sepharose™ chromatography beads). Lysine Sepharose binds angiostatin and has been used for its purification (O'Reilly et al., 1996). The endothelial cell inhibitory activity was found only in the flow-through fraction and not in the bound fraction (data not shown). The lack of binding of the inhibitory activity to lysine Sepharose suggested that the novel inhibitor of endothelial cell proliferation was not angiostatin.

EXAMPLE 3
Purification of a 20 kDa Protein from the Conditioned Media of EOMA Cells which Specifically inhibits Endothelial Cell Proliferation Because several angiogenesis inhibitors have an affinity for heparin, we applied the flow-through from the lysine Sepharose column to a heparin Sepharose column. The inhibitory activity bound heparin with relatively high affinity and was eluted with 0.6–0.8M NaCl in 10 mM Tris pH 7.4, as shown in FIG. 2. To further purify the inhibitory activity, the sample was concentrated and applied to a gel filtration (Bio-Rad Bio-Gel P-100 fine gel or Pharmacia Sephacryl S-200HR gel) column (see FIG. 3), followed by several cycles of reverse-phase HPLC with a C4 column. The inhibitory activity was eluted from the C4 column with 40–45% acetonitrile in 0.1% trifluoroacetic acid, as exemplified by FIG. 4. After the final C4 column, the inhibitory activity was associated with a protein of molecular mass of approximately 20 kDa (reduced) or 18 kDa (non-reduced), by SDS-PAGE, purified to apparent homogeneity.

With respect to Examples 2 and 3, lysine Sepharose, heparin Sepharose, Sephacryl S-200 HR gel (Pharmacia, Uppsala, Sweden), Bio-Gel P-100 fine polyacrylamide gel (Bio-Rad Laboratories, Richmond, Calif.), and a SynChropak RP-4 (100×4.6 mm) C4 reverse-phase column (Synchrom, Inc., Lafayette, Ind.) were prepared according to the manufacturers recommendations. A heparin-Sepharose column (50×2.5 cm) was equilibrated with 50 mM NaCl 10 mM Tris-HCl pH 7.4. Pooled conditioned media was applied and the column was washed with the equilibration buffer. The column was eluted with a continuous gradient of 50 mM–2M NaCl in 10 mM Tris-HCl at pH 7.4 (200 ml total volume) followed by 100 ml of 2M NaCl in 10 mM Tris-HCl at pH 7.4. Fractions were collected and an aliquot of each was applied to capillary endothelial cells. Fractions which inhibited their proliferation were dialyzed (MWCO=6,000–8,000) against PBS and concentrated using a 4000 MWCO Nanospin concentrator (Gelman Sciences, Ann Arbor, Mich.).

A Bio-Gel P-100 column or a Sephacryl S-200 HR column (75×1.5 cm) was equilibrated with PBS. The sample from heparin Sepharose chromatography was applied and the column was fluted with the equilibration buffer. Fractions were collected and an aliquot of each was applied to endothelial cells. Fractions which inhibited endothelial proliferation were concentrated and dialyzed as above.

A SynChropak RPG (100×4.6 mm) column was equilibrated with $H_2O$/0.1% trifluoroacetic acid (TFA). HPLC-grade reagents (Pierce, Rockford, Ill.) were used. The sample from gel filtration chromatography was applied to the column and the column was fluted with a gradient of acetonitrile in 0.1% TFA at 0.5 ml/minute and fractions were collected. An aliquot of each was evaporated by vacuum centrifugation, resuspended in PBS, and applied to capillary endothelial cells. Inhibitory activity was further purified to apparent homogeneity by at least two subsequent cycles on the SynChropak C4 column.

To further characterize the 20 kDa inhibitor, we tested it on several cell lines of endothelial and non-endothelial origin. For the BCE assay, bovine capillary endothelial cells were obtained and grown as previously described (Folkman et al., 1979). For the proliferation assay, cells were washed with PBS and dispersed in a 0.05% solution of trypsin. A cell suspension (25,000 cells/ml) was made with DMEM +10% BCS +1% GPS, plated onto gelatinized 24-well culture plates (0.5 mewed), and incubated (37° C., 10% $CO_2$) for 24 hours. The media was replaced with 0.25 ml of DMEM +5% BCS +1% GPS and the test sample applied. After 20 minutes of incubation, media and bFGF were added to obtain a final volume of 0.5 ml of DMEM +5% BCS +1% GPS +1 ng/ml bFGF. After 72 hours, cells were dispersed in trypsin, resuspended in Hematall (Fisher Scientific, Pittsburgh, Pa.), and counted by Coulter counter.

Non-Endothelial Cell Proliferation Assays

Bovine aortic smooth muscle (SMC), bovine retinal pigment epithelial (RPE), mink lung epithelial (MLE), Lewis lung carcinoma (LLC), and EOMA cells and 3T3 fibroblasts were maintained in a 10% CO2 and 37° C. incubator. For the proliferation assays, cells were washed with PBS and were dispersed in a 0.05% solution of trypsin. Optimal conditions for the cell proliferation assays were established for each different cell type. Fetal calf serum (FCS) was used for the RPE, MLE, and LLC cells and BCS was used for the other cell types. A cell suspension (20,000 cells/ml for SMC, RPE, MLE; 15,000 cells/ml for 3T3; 10,000 cells/ml for LLC, EOMA) was made with DMEM +10% bovine serum +1% GPS, plated onto 24-well culture plates (0.5 ml/well), and incubated (37° C., 10% C02) for 24 hours. The media was replaced with 0.5 ml of DMEM +5% bovine serum +1% GPS and the test sample applied. After 72 hours, cells were dispersed in trypsin, resuspended in Hematall (Fisher Scientific, Pittsburgh, Pa.), and counted by Coulter counter.

Only endothelial cells were significantly inhibited, as shown in Table 2.

TABLE 2

EFFECT OF ENDOSTATIN ON ENDOTHELIAL
AND NON-ENDOTHELIAL CELL PROLIFERATION

| INHIBITED | NON-INHIBITED |
|---|---|
| Bovine capillary endothelial cells | Bovine aortic smooth muscle cells |
| | Bovine retinal pigment epithelial cells |
| | 3T3 fibroblasts |
| | Mink lung epithelial cells |
| | EOMA hemangioendothelioma cells |
| | Lewis Lung carcinoma cells |

The inhibition was first observed at doses of 100 ng/ml with maximal inhibition observed at doses of 600 ng/ml or greater. No significant inhibition was seen for cells of non-endothelial origin at doses 1 log unit higher than those used to inhibit capillary endothelial cell proliferation (data not shown).

EXAMPLE 4
Microsequence Analysis of the 20 kDa Protein Reveals Identity to a Fragment of Collagen XVIII The 20 kDa inhibitor of capillary endothelial cell proliferation from the conditioned media was purified to homogeneity, as described in the above examples, resolved by SDS-PAGE, electroblotted onto PVDF (Bio-Rad, Richmond, Calif.), detected by Ponceau S stain, and excised from the membrane. N-terminal sequence was determined by automated Edman degradation on an PE/ABD Model 470A protein sequencer (Foster City, Calif.) operated with gas-phase delivery of trifluoracetic acid.

Sequence library searches and alignments were performed against combined GenBank, Brookhaven Protein, SWISS-PROT, and PIR databases. Searches were performed at the National Center for Biotechnology Information through the use of the BLAST network service.

Microsequence analysis of the inhibitor revealed identity to a C-terminal fragment of collagen XVIII. The molecular cloning and sequence of collagen XVIII was first described by Olsen and his coworkers and by Rehn and Pihlajaniemi (Oh et al., 1994; Rehn and Pihlajaniemi, 1994). Collagen XVIII is a novel collagen which consists of an N-terminal region with 3 splice variants (Muragaki et al., 1995; Rehn and Pihlajaniemi, 1995), a series of collagen-like domains with interruptions, and a 35 kDa C-terminal non-collagenous (NC1) domain. An 18-amino acid N-terminal microsequence analysis of the purified inhibitor of endothelial cell proliferation confirms that it is identical to a C-terminal fragment of this NC1 domain (FIG. 5). We have named this inhibitory fragment of collagen XVIII "endostatin" and it is included in the group of molecules that have endostatin activity.

EXAMPLE 5
Recombinant Mouse Endostatin (Baculovirus or E. coli) Inhibits Endothelial Cell Proliferation In Vitro and Angiogenesis In Vivo The endothelial proliferation cell inhibitor of the present invention can be recombinantly expressed in any system used to express proteins. Non-limiting examples of such expressions systems include bacterial expression systems, yeast expression systems and insect viral expression systems.

Recombinant mouse endostatin was expressed using the BacPAK baculovirus expression system (CLONTECH Laboratories) following the manufacture's protocol. Briefly, a cDNA fragment encoding the signal sequence and C-terminal part (endostatin region) of mouse collagen XVIII was inserted into the pBacPAK8 transfer vector. BacPAK6 viral DNA (expression vector) and plasmid DNA of the pBacPAK8-endostatin clone (modified transfer vector) were then cotransfected into insect Sf21 cells and media containing expressed mouse endostatin was collected. The BacPAK6 was first digested with BSU36 enzyme to make it incompetent for independent replication. The media containing expressed mouse endostatin was applied to a 1.5×40 cm heparin Sepharose column which had been equilibrated with 50 mM NaCl 10 mM Tris pH 7.4. The column was washed with the equilibration buffer and was then eluted sequentially with 0.2M NaCl, 0.4M NaCl, 0.6M NaCl, and 1M NaCl in 10 mM Tris pH 7.4. All chromatography was performed at 4° C. The 0.6M NaCl eluant (which inhibited bovine capillary endothelial cells in a 72 hour proliferation assay) was dialyzed (6–8000 MWCO) against PBS and then reapplied to the heparin Sepharose column. The column was eluted with a gradient of 50 mM NaCl–1.2M NaCl in 10 mM Tris pH 7.4. An aliquot of each fraction was applied to bovine capillary endothelial cells as above and fractions which inhibited proliferation were pooled, dialyzed against PBS, and concentrated using a Nanospin Plus (Gelman Sciences) centrifugal concentrator (MWCO=10,000). SDS-PAGE of the concentrated sample revealed a discrete band of apparent $M_r$ of 20 kDa.

Expression and Purification of Recombinant Mouse Endostatin from *E. coli*

The C-terminal part of the cDNA of collagen XVIII was used to amplify the cDNA of mouse endostatin which was cloned into the pETKH1 vector (pET11d derivative) (Studier et al., 1990). Induction resulted in the production of a fusion protein carrying the amino acid sequence MARRASVGTD SEQ ID NO: 2 (RRAS=protein kinase A recognition sequence) and 6 histidine residues at the N-terminus followed by the sequence of mouse endostatin (pTB01#8). The pTB01#8 plasmid was transformed into BL21:DE3 and the fusion protein was purified on $Ni^{+2}$-NTA-beads as described (QiaExpressionist Handbook, Qiagen). Briefly, *E. coli* were grown until an $O.D._{600}$ of 0.8–0.9 and expression of the fusion protein was then induced for 3 hours with 1 mM IPTG. The bacteria were pelleted and resuspended in 8M urea, 10 mM Tris-HCl pH 8.0 containing 10 mM imidazole and incubated for 1 hour at room temperature. The suspension was centrifuged for 15 minutes at 20,000 g and the supernatant incubated with the $Ni^{+2}$-NTA beads for 1 hour at room temperature. The suspension was transferred into a column and washed with 8M urea, 0.1M Na-phosphate, 10 mM Tris-HCl pH 6.25 containing 10 mM imidazole. The protein was eluted with the same buffer containing 250 mM imidazole. The fractions containing endostatin were extensively dialyzed against PBS. During dialysis, the endostatin precipitated. The precipitated endostatin was resuspended in PBS, the protein concentration was adjusted to 2–4 mg/ml, and the endostatin was stored at $-20°$ C. until use. For the mouse studies, endostatin was delivered as a suspension in PBS. For the chick chorioallantoic assay, endostatin was further dialyzed against water and then lyophilized.

Recombinant mouse endostatin was produced in both baculovirus and *E. Coli* expression systems. Using sequential heparin Sepharose chromatography, recombinant mouse endostatin was purified to apparent homogeneity from insect cell media. $Ni^{+2}$-NTA-agarose was used to purify the *E. coli*-derived mouse endostatin.

SDS-PAGE revealed a discrete band of approximately 20 kDa or approximately 22 kDa (reduced) purified to apparent homogeneity for baculovirus and *E. coli*-derived recombinant endostatins, respectively (data not shown). Both were dialyzed against PBS prior to use. After dialysis, the material from the *E. coli* system precipitated and was delivered as a suspension for subsequent in vivo studies. Recombinant endostatin from baculovirus specifically inhibited the proliferation of bovine capillary endothelial cells in a dose-dependent fashion. The inhibition was seen at doses of 100 ng/ml with maximal inhibition observed at doses above 600 ng/ml. No significant inhibition of proliferation of cells of non-endothelial origin or of the EOMA cells was observed when endostatin was tested at doses up to 1 log unit higher than those used to inhibit endothelial cell proliferation.

The precipitated (un-refolded) material was not testable in vitro, because of its insolubility. However, a small percentage was soluble in PBS during dialysis and this fraction was used for the endothelial cell assays. Furthermore, after refolding, it was soluble and inhibited endothelial proliferation (data not shown). When this soluble material was applied to endothelial cells, it was found to be inhibitory at concentrations comparable to both the native and baculovirus-derived endostatin.

To test for the ability of recombinant mouse endostatin to inhibit in vivo angiogenesis, we used the chick chorioallantoic membrane (CAM) assay (Folkman, 1985; Nguyen et al., 1994 which are incorporated herein by reference). Briefly, three day old fertilized white Leghorn eggs (Spafas, Norwich, Conn.) were cracked, and embryos with intact yolks were placed in 100×20 mm petri dishes (Folkman, 1985). After 3 days of incubation ($37°$ C. and 3% $CO_2$), a methylcellulose (Fisher Scientific, Fair Lawn, N.J.) disc containing endostatin was applied to the CAM of individual embryos. The discs were made by desiccation of endostatin in 10 μl of 0.45% methylcellulose (in $H_2O$) on teflon rods. After 48 hours of incubation, embryos and CAMs were observed by means of a stereomicroscope.

At doses of 10–20 μg/10 μl disc, there was potent inhibition of in vivo angiogenesis for both the *E. coli* and the baculovirus-derived endostatins in all of the tested CAMs (n=5/group). The *E. coli* derived-endostatin precipitate gradually dissolved over 5 days and produced a sustained antiangiogenic effect on the implanted CAMs. In contrast, the soluble baculovirus-derived endostatin dissolved within 24 hours and gave a maximal antiangiogenic effect within a period of 48 hours. There was no evidence of toxicity in any of the chick embryos tested.

Human Endostatin was produced recombinantly using similar methods.

EXAMPLE 6
Recombinant Mouse Endostatin Inhibits the Growth of Metastases

Because tumor growth is angiogenesis dependent, we treated Lewis lung carcinoma metastases systematically with recombinant mouse endostatin expressed in the baculovirus system. Animals with Lewis lung carcinomas of 600–1200 $mm^3$ tumors were sacrificed and the skin overlying the tumor was cleaned with betadine and ethanol. In a laminar flow hood, tumor tissue was excised under aseptic conditions. A suspension of tumor cells in 0.9% normal saline was made by passage of viable tumor tissue through a sieve and a series of sequentially smaller hypodermic needles of diameter 22- to 30-gauge. The final concentration was adjusted to 1×107 cells/ml and the suspension was placed on ice. After the site was cleaned with ethanol, the subcutaneous dorsa of mice in the proximal midline were injected with 1×106 cells in 0.1 ml of saline.

When tumors were 1500 $mm^3$ in size, approximately 14 days after implant, the mice underwent surgical removal of the tumor. The incision was closed with simple interrupted sutures. From the day of operation, mice received daily intraperitoneal injections of recombinant (baculovirus) mouse endostatin or saline. Mice received 0.3 mg/kg/day of endostatin once daily via subcutaneous injection. When the control mice became sick from metastatic disease (i.e., after 13 days of treatment), all mice were sacrificed and autopsied. Lung surface metastases were counted by means of a stereomicroscope at 4× magnification.

The growth of Lewis lung carcinoma metastases was almost completely suppressed by the systemic administration of endostatin at a dose of 0.3 mg/kg/day given subcutaneously (7±3 metastases/mouse, n=4, $p<0.001$). In contrast, in mice treated with saline after removal of a Lewis lung carcinoma primary tumor, lung metastases grew rapidly (77±7 metastases/mouse). Lung weight, which reflects tumor burden, was 240±25 mg in the endostatin treated mice versus 760±30 mg in the control mice ($p<0.001$). Further, there was no weight loss or evidence of toxicity in any of the mice treated with endostatin.

EXAMPLE 7
Recombinant Mouse Endostatin Inhibits the Growth of Primary Tumors The yield of endostatin from the baculovirus system was lower than that of the *E. coli* system, i.e. 1–2 mg/liter versus 30–40 mg/liter. We therefore used *E. coli*-derived endostatin to study the effect of endostatin therapy on primary tumor growth. We produced recombinant mouse endostatin from *E. coli* in sufficient quantity to treat Lewis lung carcinoma primary tumors. The endostatin was administered as a suspension of the precipitated purified protein to mice bearing Lewis lung carcinomas of at least 100–200 mm$^3$. The protein was purified by conventional means but was not refolded prior to its administration to the mice. The injected precipitate was slowly resorbed over 24–48 hours.

We are unaware of any precedent for the use of an injected depot of non-refolded recombinant protein as a sustained-release method in animals. Nevertheless, endostatin gradually resorbed in vivo and proved to have potent antiangiogenic activity which resulted in prolonged anti-tumor and antiangiogenic activity. Therefore, these data suggest a novel general method for the controlled release of recombinant proteins. Based on this rationale, we have delivered non-refolded recombinant angiostatin from *E. coli* with similar success.

Accordingly, an aspect of the invention is the administration of recombinant endostatin or endostatin analogs in an un-refolded state so as to provide a sustained release depot of endothelial cell proliferation inhibiting protein over a period of at least 8 hours, desirably at least 12 hours, more desirably at least 24 hours or at least 48 hours, depending on the patient and the disease to be treated. Optionally recombinant and un-refolded angiostatin is administered to similarly provide a sustained release depot of protein capable of releasing angiostatin protein over a period of at least 8 hours, desirably at least 12 hours, more desirably at least 24 hours or at least 48 hours, depending on the patient and the disease to be treated.

Mice were implanted with Lewis lung carcinomas as described above. Tumors were measured with a dial-caliper and tumor volumes were determined using the formula width$^2$ × length ×0.52, and the ratio of treated to control tumor volume (T/C) was determined for the last time point. After tumor volume was 100–200 mm$^3$ (0.5–1% of body weight), which occurred within 3–7 days, mice were randomized into two groups. One group received recombinant mouse endostatin (*E. coli*) as a suspension in PBS injected subcutaneously at a site distant from the tumor once daily. The other group received comparable injections of the vehicle alone. The experiments were terminated and mice were sacrificed and autopsied when the control mice began to die.

The growth of Lewis lung primary tumors was potently suppressed by systemic therapy with endostatin. Increasing the dose of endostatin was associated with improved efficacy (data not shown). At a dose of 10 mg/kg, tumor growth was inhibited by 97% as compared to control mice treated with vehicle alone. At a dose of 20 mg/kg given once daily, in two separate experiments, there was an almost complete regression of established primary tumors (>99% inhibition, p<0.001). These surprising and unexpected results are shown in FIGS. 6 and 7.

FIGS. 8, 9, 10 and 11 demonstrate the effectiveness of recombinant mouse endostatin for inhibiting tumor growth in a variety of different tumor models. Also demonstrated is the effectiveness of endostatin derived from human for inhibiting tumor growth.

Immunohistochemical analysis (FIG. 12) of the residual small tumors showed a potent inhibition of angiogenesis in the endostatin treated tumors. Further, the proliferative index of tumors in the endostatin and saline treated mice was at the same high level in both groups while the apoptotic index increased 8-fold after endostatin therapy. Thus, endostatin therapy results in a similar pattern of tumor dormancy to the one we have previously described for angiostatin (Holmgren et al., 1995; O'Reilly et al., 1996). Further, there was no evidence of drug-related toxicity in any of the treated mice.

After discontinuation of endostatin therapy, a tumor recurred at the primary site within 5–14 days, became vascularized, and eventually killed the mice (data not shown). Notably, we found that *E. coli*-derived recombinant mouse endostatin with a C-terminal polyhistidine tag, which was expressed, purified and administered in a comparable fashion to the N-terminal tagged product described above did not inhibit angiogenesis in the CAM assay and had no effect on the growth of Lewis lung carcinomas (data not shown). These data argue strongly that the anti-tumor and antiangiogenic activity of recombinant endostatin are due to the specific structure of endostatin and not to a contaminant in the sample.

FIG. 13 shows the results of cycled treatment of Lewis lung carcinoma with recombinant mouse endostatin derived from *E. coli*. These results clearly show reproducible endostatin-dependent regression of tumor mass, followed by tumor growth after termination of endostatin treatment.

These results show that a murine hemangioendothelioma produces a novel and specific 20 kDa inhibitor of endothelial cell proliferation in vitro which is also a potent inhibitor of angiogenesis and tumor growth in vivo. The N-terminal sequence of this inhibitor, endostatin, is identical to a C-terminal fragment of collagen XVIII. Systemic administration of recombinant endostatin potently inhibits angiogenesis, maintains metastases at a microscopic size, and regresses primary tumors to less than 1 mm$^3$, a reduction of over 150-fold. For as long as mice are treated there is no regrowth of tumors, no evidence of drug resistance, and no toxicity. It is interesting to note that some fragments of the C-terminal domain of collagen type XVIII that are longer than endostatin do not inhibit endothelial cell proliferation (data not shown).

Endostatin was discovered by the same strategy employed to find angiostatin (O'Reilly et al.,1994), i.e., isolation from a tumor. While it is counter-intuitive that tumors should be a source of angiogenesis inhibitors, the results reported here seem to validate this approach.

This leads to the question of why angiogenesis inhibitors should be present in tumors that are angiogenic. One possibility is that an inhibitor could be 'left-over' after downregulation of its production by a tumor cell undergoing the switch to the angiogenic phenotype. This appears to be the case for thrombospondin produced by Li-Fraumeni cells in which the second allele for p53 is mutated or deleted (Dameron et al., 1994).

A second possibility is that the proteolytic activity which accompanies tumor growth, and which is an important component of capillary blood vessel growth, may also mobilize circulating angiogenesis inhibitors from precursor proteins which are not inhibitory themselves. Angiostatin for example, inhibits angiogenesis and endothelial cell proliferation while plasminogen does not (O'Reilly et al., 1996; O'Reilly et al., 1994). For endostatin, a similar pattern is revealed.

Histology of tumors which regressed under endostatin therapy showed perivascular cuffing of tumor cells surrounding one or more microvessels in which angiogenesis was blocked. Tumor cells displayed high proliferation balanced by high apoptosis, with no net gain in tumor size. These data are consistent with a model of a new type of tumor dormancy recently proposed (Holmgren et al., 1995). Furthermore, endostatin inhibited proliferation of endothelial cells in vitro, but had no effect on Lewis lung carcinoma cells, or other cell types including smooth muscle, epithelium, fibroblasts, and the EOMA cell line from which it was purified.

The fact that a specific inhibitor of endothelial cell proliferation can regress a tumor to a microscopic size and hold it in a dormant state, despite the fact that the tumor cells are refractory to the inhibitor from the outset, indicates that the endothelial population can exert powerful growth regulatory control over the tumor cells.

The results with endostatin support the theory (Folkman, 1996) that for therapeutic purposes, it is fruitful to think about a tumor in terms of two distinct cell populations: a tumor cell population and an endothelial cell population, each of which can stimulate growth of the other. Growth of each cell population may be optimally inhibited by agents which selectively or specifically target that cell type, i.e., cytotoxic chemotherapy and antiangiogenic therapy. Furthermore, combined treatment of both cell populations may be better than treatment of either cell type alone.

To test this theory mice seeded with Lewis lung carcinomas, and bearing tumors which had attained a size of approximately 300 mm$^3$, were treated with a combination therapy comprising angiostatin and endostatin, each at a dose of 20 mg/kg/day for 25 days. Tumors regressed to microscopic levels by about day 10 of treatment. A completely unexpected finding was that tumors remained regressed and dormant for approximately three months, even after all treatment was terminated, as is shown in FIG. 14. Experiments of longer duration indicate that an initial treatment of tumor with a combination of angiostatin and endostatin causes a very long term dormancy, the actual period of which is unknown at this time.

Such long term dormancy is considered a cure to one skilled in the art. For example, the NIH guideline for determining when a treatment is effective as a cancer cure, is that the tumor remain dormant (i.e. not increasing in size) for ten times the normal doubling time of the tumor. The dormancy length achieved using a combination of endostatin and angiostatin far exceeds this criteria.

Accordingly, an important aspect of the invention is a composition comprising a combination of angiostatin and endostatin, or an endostatin analog, in amounts sufficient to cause long term dormancy, or cure, of angiogenesis-dependent cancers when administered to patients with angiogenesis-dependent cancers. Administration can be systemically, for example by injection, in which case the dosage is determined depending upon the patient and the particular cancer, but which generally is at least 0.2 mg/kg/day, desirably at least 2.0 mg/kg/day, more desirably at least 20 mg/kg/day. Generally, the composition is administered daily for at least 10 days, desirably at least 20 days, more desirably at least 25 days. Alternative systemic administration routes include, orally where the composition is formulated, for example into coated microbeads, to protect the protein from inactivating digestive environments; transdermally; and via pump.

Alternatively, different dosages and treatment periods can be used if the composition is administered locally to an angiogenesis-dependent site, such as a tumor. Such administration may be, for example, surgical implantation or local injection into, or near by, the site.

EXAMPLE 8

Isolation of the putative receptor for endostatin.

Both endostatin and angiostatin appear to be specific inhibitors of endothelial cell proliferation. Therefore, it is likely that endostatin binds to specific structures exclusively expressed on the surface of endothelial cells. We are not aware of the existence of any other specific inhibitors of endothelial cell proliferation.

Identifying and isolating proteins which specifically bind to endostatin is accompanied by methods well known in the art, for example by affinity chromatography and expression cloning.

Affinity chromatography. Bovine Capillary Endothelial cells (BCE) are radiolabeled with [35S]-methionine, total cell and membrane extracts prepared and applied to affinity columns prepared with endostatin. As a negative control, fibroblast protein extracts are isolated in a similar way. Bound proteins are eluted from the column using a NaCl gradient and the different fractions are analyzed using standard SDS-PAGE and autoradiography. This procedure yields proteins that are tightly bound to the endostatin column and present only in the endothelial cell derived fractions. Comparing the gel electrophoretic patterns of the two cell types reveals expressed proteins unique to the BCE cells. Protein sequences subsequently are determined and corresponding gene(s) cloned. A cDNA library of bovine capillary endothelial cells, is prepared and screened with a degenerative oligo based PCR technique to locate the cDNA(s) of the endostatin- specific binding protein(s). Hybridization using degenerative oligonucleotides to the corresponding cDNA, is also used to identify genes of endostatin binding proteins. Another approach is to raise antibodies against the peptide sequences with methods described earlier in the Detailed Description and immunoscreen the same library.

Expression cloning. A cDNA library of BCE cells is prepared. Poly-A mRNA is isolated from BCE cells whose proliferation has previously been inhibited by endostatin. These cells express an endostatin binding protein. The corresponding cDNA library is transfected into cells allowing high expression of the various cDNAs. Binding activity of endostatin to cells which express the receptor protein on the surface is used as a positive selection of these cells. To select for these cells, purified endostatin is labeled with biotin and consequently detected using either streptavidin coupled magnetic-beads or FACS sorting. Alternatively, an antibody against endostatin is used for screening. After selection of the positive cells, the corresponding plasmids are isolated, amplified and transfected again into high expression cells. After several rounds of positive selection, plasmids are analyzed for identical inserts using endonuclease digestion and PCR. Using these data, complementation groups are formed, sequenced and analyzed with the BLAST network program. In addition to computer analysis, individual cDNAs are re-transfected into high expression cells and tested for endostatin binding activity under different conditions (e.g., competition with non-labeled endostatin, time-course of binding, Scatchard analysis, etc. in other words the use of "classical" receptor characterization procedures known to those skilled in the art).

EXAMPLE 9

Determination of the minimal region of the mouse endostatin protein responsible for its antiangiogenic activity.

Different PCR primers are designed, the corresponding cDNAs cloned into the *E. coli* expression system, and the different endostatin fragments purified to homogeneity. The full length cDNA is cut from both the N- and C-terminus. As a first screen the capillary endothelial proliferation assay and the chick embryo assay are used to determine the residual activity compared to the full length fragment.

EXAMPLE 10

Determination of the putative enzyme(s) which may release endostatin from collagen XVIII.

Collagen XVIII belongs to the non-fibrillar collagen type family and can be found in three different splicing variants encoding for proteins with 1315-, 1527-, and 1774 amino acid residues (Rehn, PNAS 91:4234, 1994). The difference is caused by alterations in the N-terminal part of the gene and therefore all three splicing variants could potentially be the source of endostatin which itself is a fragment of the non—collagenous domain 11 (NC11). The function of collagen XVIII is not known, but because its message is substantially expressed in highly vascularized organs, a role in perivascular matrix assembly and/or structure has been proposed (Oh, et al., Genomics, 19:494, 1994). A first clue about the function of collagen XVIII came from the purification of endostatin as a potent inhibitor of endothelial cell proliferation.

From this preliminary data and from our initial observation that endostatin was purified from conditioned medium of a hemangioendothelioma (EOMA), we asked whether the enzyme(s) which release endostatin from collagen XVIII could be identified.

The last 325 amino acid residues, encoding for the NC11 domain, are expressed in *E. coli* and the insect cell baculovirus system, the purified protein is used as a substrate to identify enzymes that clone this region of collagen XVIII. By PCR, a cDNA fragment encoding the NC11 domain is cloned into an *E. coli* expression vector (pET series) which allows high expression of the target protein after induction with IPTG. Alternatively, a vector suitable for insect cell expression is used. The proteins are tagged with the $HIS_6$-Tag located on the C-terminus for purification using $Ni^{2+}$-NTA-beads. An $Ni^{2+}$-NTA-alkaline phosphatase conjugate can detect the C-terminus by Western blotting. Another construct is made which not only has a $HIS_6$-Tag on the C-terminus, but will also encode the hemagglutinin (HA-tag on the N-terminus. This is detected by Western blotting with an HA-specific monoclonal antibody. The N- and C-terminus of the protein followed after incubation with EOMA supernatant and different metalloproteinase extracts.

Cleavage product is detected by SDS-PAGE analysis or Western blotting, the protein is re-purified using the $Ni^{2+}$-NTA beads, eluted with imidazole, dialyzed against PBS and tested for inhibitor activity in the various in vitro and in vivo assays (e.g., endothelial cell proliferation, chick embryo, and mouse corneal assay). If the purified cleavage product shows inhibitory activity, N-terminal amino acid sequencing is performed and compared to the original starting sequence of endostatin obtained from the EOMA supernatant. Accordingly, the cleavage procedure can be scaled up to purify sufficient protein for testing in tumor-bearing mice, and to compare this activity to that of the full length NC11 domain.

References

The following references are hereby incorporated by reference herein in their entirety.

Angiolillo, A. L., Sgadari, C., Taub, D. D., Liao, F., Farber, J. M., Miaheshwari, S., Kleinman, H. K., Reaman, G. H., and Tosato, G. (1995). Human interferon-inducible protein 10 is a potent inhibitor of angiogenesis in vivo. J. Exp. Med. 182, 155–162.

Cao, Y., Chen, C., Weatherbee, J. A., Tsang, M., and Folkman, J. (1995). Gro-beta, a C-X-C chemokine, is an angiogenesis inhibitor that suppresses the growth of Lewis lung carcinoma in mice. J. Exp. Med. 182, 2069–2077.

Chen, C., Parangi, S., Tolentino, M. J., and Folkman, J. (1995). A strategy to discover circulating angiogenesis inhibitors generated by human tumors. Cancer Res. 55, 4230–4233.

Clapp, C., Martial, J. A., Guzman, R. C., Rentier-Delrue, F., and Weiner, R. 1. (1993). The 16-kilodalton N-terminal fragment of human prolactin is a potent inhibitor of angiogenesis. Endocrinology 133, 1292–1299.

Dameron, K. M., Volpert, O. V., Tainsky, M. A., and Bouck, N. (1994). Control of angiogenesis in fibroblasts by p53 regulation of thrombospondin-1. Science 265, 1582.

Folkman, J. (1996). Tumor angiogenesis and tissue factor. Nature Med. 2, 167–168.

Folkman, J. (1989). What is the evidence that tumors are angiogenesis dependent?. J. Natl. Cancer Inst. 82, 4–6.

Folkman, J. (1985). Angiogenesis and its inhibitors. In Important Advances in Oncology 1985, V. T. DeVita, S. Hellman, and S. Rosenberg, eds. (Philadelphia: J. B. Lippincott Company), pp. 42–62.

Folkman, J., Haundenschild, C. C., and Zetter, B. R. (1979). Long-term culture of capillary endothelial cells. Proc. Natl. Acad. Sci. USA 76, 5217–5221.

Gavrieli, Y., Sherman, Y., and Ben-Sasson, S. A. (1992). Identification of programmed cell death in situ via specific labeling of nuclear DNA fragmentation. J. Cell Biol. 119, 493–501.

Good, D. J., Polverini, P. J., Rastinejad, F., Le Beau, M. M., Lemons, R. S., Frazier, W. A., and Bouck, N. P. (1990). A tumor suppressor-dependent inhibitor of angiogenesis is immunologically and functionally indistinguishable from a fragment of thrombospondin. Proc. Nat. Acad. Sci. USA. 87, 6624–6628.

Grant, D. S., Tashiro, K.-l., Sequi-Real, B., Yamada, Y., Martin, G. R., and Kleinman, H. K. (1989). Two different laminin domains mediate the differentiation of human endothelial cells into capillary-like structures in vitro. Cell 58, 933–943.

Gross, J. L., Moscatelli, D., and Rifkin, D. B. (1983). Increased capillary endothelial cell protease activity in response to angiogenic stimuli in vitro. Proc. Natl. Acad. Sci. USA 80, 2623–2627.

Gupta, S. K., Hassel, T., and Singh, J. P. (1995). A potent inhibitor of endothelial cell proliferation is generated by proteolytic cleavage of the chemokine platelet factor 4. Proc. Natl. Acad. Sci. USA 92, 7799–7803.

Holmgren, L., O'Reilly, M. S., and Folkman, J. (1995). Dormancy of micrometastases: balanced proliferation and apoptosis in the presence of angiogenesis suppression. Nature Med. 1, 149–153.

Homandberg, G. A., Williams, J. E., Grant, D., B., S., and Eisenstein, R. (1985). Heparin-binding fragments of fibronectin are potent inhibitors of endothelial cell growth. Am. J. Path. 120, 327–332.

Hori, A., Sasada, R., Matsutani, E., Naito, K., Sakura, Y., Fujita, T., and Kozai, Y. (1991). Suppression of solid tumor growth by immunoneutralizing monoclonal antibody against human basic fibroblast growth factor. Cancer Res. 51, 6180–6184.

Kandel, J., Bossy-Wetzel, E., Radvany, F., Klagsburn, M., Folkman, J., and Hanahan, D. (1991). Neovascularization is associated with a switch to the export of bFGF in the multistep development of fibrosarcoma. Cell 66, 1095–1104.

Kim, K. J., Li, B., Winer, J., Armanini, M., Gillett, N., Phillips, H. S., and Ferrara, N. (1993). Inhibition of vascular endothelial growth factor-induced angiogenesis suppresses tumor growth in vivo. Nature 362, 841–844.

Maione, T. E., Gray, G. S., Petro, J., Hunt, A. J., Donner, A. L., Bauer, S. I., Carson, H. F., and Sharpe, R. J. (1990). Inhibition of angiogenesis by recombinant human platelet factor-4 and related peptides. Science 247, 77–79.

Millauer, B., Shawver, L. K., Plate, K. H., Risau, W., and Ullrich, A. (1994). Glioblastoma growth inhibited in vivo by a dominant-negative Flk–1 mutant. Nature 367, 576–579.

Muragaki, Y., Timmons, S., Griffith, C. M., Oh, S. P., Fadel, B., Quertemmous, T., and Olsen, B.- R. (1995). Mouse col18a1 is expressed in a tissue-specific manner as three alternative variants and is localized in basement membrane zones. Proc. Natl. Acad. Sci. USA 92, 8763–8767.

Nelson, J., Allen, W. E., Scott, W. N., Bailie, J. R., Walker, B., and McFerran, N. V. (1995). Murine epidermal growth factor (EGF) fragment (33–42) inhibits both EGF- and laminin-dependent endothelial cell motility and angiogenesis. Cancer Res. 55, 3772–3776.

Nguyen, M., Shing, Y., and Folkman, J. (1994). Quantitation of angiogenesis and antiangiogenesis in the chick embryo chorioallantoic membrane. Microvascular Res. 47, 31–40.

O'Reilly, M. S., Holmgren, L., Chen, C. C., and Folkman, J. (1996). Angiostatin induces and sustains dormancy of human primary tumors in mice. Nature Med. 2, 689–692.

O'Reilly, M. S., Holmgren, L., Shing, Y., Chen, C., Rosenthal, R. A., Moses, M., Lane, W. S., Cao, Y., Sage, E. H., and Folkman, J. (1994). Angiostatin: A novel angiogenesis inhibitor that mediates the suppression of metastases by a Lewis lung carcinoma. Cell 79, 315–328.

Obeso, J., Weber, J., and Auerbach. R. (1990). A hemangioendothelioma-derived cell line: its use as a model for the study of endothelial cell biology. Lab. Invest. 63, 259–269.

Oh, S. K., Kamagata, Y., Muragaki, Y., Timmons, S., Ooshima, A., and Olsen, B. R. (1994). Isolation and sequencing of cDNAs for proteins with multiple domains of GlyXaa-Yaa repeats identify a distinct family of collagenous proteins. Proc. Natl. Acad. Sci. USA 91, 4229–4233.

Parangi, S., O'Reilly, M., Christofori, G., Holmgren, L., Grosfeld, J., Folkman, J., and Hanahan, D. (1996). Anti-angiogenic therapy of transgenic mice impairs de novo tumor growth. Proc. Natl. Acad. Sci. USA 93, 2002–2007.

Rastinejad, F., Polverini, P. J., and Bouck, N. P. (1989). Regulation of the activity of a new inhibitor of angiogenesis by a cancer suppressor gene. Cell 56, 345–355.

Rehn, M., and Pihlajaniemi, T. (1994). a1(XVIII), a collagen chain with frequent interruptions in the collagenous sequence, a distinct tissue distribution, and homology with type XV collagen. Proc. Natl. Acad. Sci. USA 91, 4234–4238.

Rehn, M., and Pihlajaniemi, T. (1995). Identification of three N-terminal ends of type XVIII collagen chains and tissue-specific differences in the expression of the corresponding transcripts. J. Biol. Chem. 270, 4705–4711.

Sage, E. H., Bassuk, J. A., Vost, J. C., Folkman. M. J., and Lane, T. F. (1995). Inhibition of endothelial cell proliferation by SPARC is mediated through a Ca (2+)-binding EF-hand sequence. J. Cell Biochem. 57, 127–140.

Sakamato, N., Iwahana, M., Tanaka, N. G., and Osaka, 8. (1991). Inhibition of angiogenesis and tumor growth by a synthetic laminin peptide, CDPGYIGSR-NH$_2$. Cancer Res. 51, 903–906.

Strieter, R. M., Kunkel, S. L., Arenberg, D. A., Burdick, M. D., and Polverini, P. J. (1995). Human interferon-inducible protein 10 (IP-10), a member of the C-X-C chemokine family, is an inhibitor of angiogenesis. Biochem. Biophys. Res. Comm. 210, 51–57.

Studier, W. F., Rosenberg, A. H., Dunn, J. J., and Dudendorf, J. W. (1990). Use of T7 RNA polymerase to direct expression of cloned genes. Methods Enzymol. 85, 60–89.

Teicher, B. A., Holden, S. A., Ara, G., Sotomayor, E. A., and Dong, H. Z. (1994). Potentiation of cytotoxic cancer therapies by TNP-470 alone and with other antiangiogenic agents. Int. J. Cancer 57, 1–6.

Tolsma, S. S., Volpert, O. V., Good, D. J., Frazier, W. A., Polverini, P. J., and Bouck, N. (1993). Peptides derived from two separate domains of the matrix protein thrombospondin-1 have antiangiogenic activity. J. Cell Biol. 122, 497–511.

Voest, E. E., Kenyon, B. M., O'Reilly, M. S., Truitt, G., D'Amato, R. J., and Folkman, J. (1995). Inhibition of angiogenesis in vivo by interleukin 12. J. Natl. Cancer Inst. 87, 581–586.

---

We claim:

1. Isolated endostatin protein having a molecular weight of approximately 18 kDa as determined by non-reducing gel electrophoresis, or approximately 20 kDa as determined by reducing gel electrophoresis, wherein the protein has an amino acid sequence of a fragment of a collagen type XVIII, a collasen type XV, or BOVMPE 1 pregastric esterase and wherein the protein is further characterized by its ability to specifically inhibit proliferating cultured endothelial cells.

2. The endostatin protein of claim 1, wherein the N-terminal amino acid sequence of the protein is shown in SEQ ID NO:1.

3. The endostatin protein of claim 1, wherein the endostatin protein has an amino acid sequence of a C-terminal peptide fragment of collagen type XVIII.

4. The endostatin protein of claim 1 made by a process comprising recombinantly producing the protein of claim 1 in a recombinant expression system, and isolating the recombinantly produced protein in its un-refolded form.

5. The endostatin protein of claim 4, wherein the recombinant expression system is *E. coli* or baculovirus.

6. The endostatin protein of claim 1, wherein the endostatin protein has an amino acid sequence of a peptide fragment of collagen type XV.

7. The endostatin protein of claim 1, wherein the endostatin protein has a amino acid sequence of a peptide fragment of BOVMPE 1 pregastric esterase.

8. A composition comprising,
angiostatin protein combined with endostatin protein having a molecular weight of approximately 18 kDa as determined by non-reducing gel electrophoresis, or approximately 20 kDa as determined by reducing gel electrophoresis, wherein the protein has an amino acid sequence of a fragment of a collagen type XVIII, a collagen type XV, or BOVMPE 1 pregastric esterase and wherein the protein is further characterized by its ability to specifically inhibit proliferating cultured endothelial cells,
wherein the angiostatin protein and the endostatin protein are provided in amounts such that the composition is capable of effectively regressing the mass of an angiogenesis-dependent tumor.

9. The composition of claim 8, wherein the endostatin protein has a N-terminal amino acid sequence shown in SEQ ID NO:1.

10. The endostatin protein of claim 8, wherein the endostatin protein has an amino acid sequence of a C-terminal peptide fragment of collagen type XVIII.

11. The composition of claim 8, wherein the endostatin protein has an amino acid sequence of a peptide fragment of collagen type XV.

12. The endostatin protein of claim 8, wherein the endostatin protein has an amino acid sequence of a peptide fragment of BOVMPE 1 pregastric esterase.

13. The composition of claim 8, wherein the angiostatin protein or the endostatin protein is made by a process comprising recombinantly producing either protein in a recombinant expression system, and isolating the recombinantly produced protein.

14. The composition of claim 13, wherein the protein is isolated in its un-refolded form.

15. The composition of claim 13, wherein the recombinant expression system is *E. coli* or baculovirus.

16. The composition of claim 8, wherein the angiostatin protein is a peptide fragment of approximately kringle regions 1–4 of a plasminogen molecule having endothelial cell proliferation inhibiting activity.

17. Isolated endostatin protein having a molecular weight of approximately 18 kDa as determined by non-reducing gel electrophoresis, or approximately 20 kDa as determined by reducing gel electrophoresis, wherein the protein is a fragment of collagen that binds to a heparin affinity column and does not bind to a lysine affinity column, and wherein the protein inhibits proliferating cultured endothelial cells.

18. The endostatin protein of claim 17, wherein the endostatin protein has a N-terminal amino acid sequence shown in SEQ ID NO:1.

19. The endostatin protein of claim 17, wherein the endostatin protein has an amino acid sequence of a C-terminal peptide fragment of collagen type XVIII.

20. The endostatin protein of claim 17, wherein the endostatin protein has an amino acid sequence of a peptide fragment of collagen type XV.

21. The endostatin protein of claim 17, wherein the endostatin protein is made by a process comprising recombinantly producing the protein in a recombinant expression system, and isolating the recombinantly produced protein.

22. The endostatin protein of claim 21 isolated in its un-refolded form.

23. The endostatin protein of claim 17, wherein the endostatin protein can be isolated from the murine hemangioendothelioma EOMA cell line.

24. A composition comprising a pharmaceutically acceptable excipient and endostatin protein having a molecular weight of approximately 18 kDa as determined by non-reducing gel electrophoresis, or approximately 20 kDa as determined by reducing gel electrophoresis, wherein the protein has an amino acid sequence of a fragment of a collagen type XVIII, a collagen type XV, or BOVMPE 1 pregastric esterase, and wherein the protein is further characterized by its ability to specifically inhibit proliferating cultured endothelial cells.

25. The composition of claim 24, wherein the endostatin protein has a N-terminal amino acid sequence shown in SEQ ID NO:1.

26. The composition of claim 24, wherein the endostatin protein has an amino acid sequence of a C-terminal peptide fragment of collagen type XVIII.

27. The composition of claim 24, wherein the endostatin protein has an amino acid sequence of a peptide fragment of collagen type XV.

28. The composition of claim 24, wherein the endostatin protein has an amino acid sequence of a peptide fragment of BOVMPE 1 pregastric esterase.

29. The composition of claim 24, wherein the endostatin protein is made by a process comprising recombinantly producing the endostatin protein in a recombinant expression system, and isolating the recombinantly produced protein.

30. A composition comprising a pharmaceutically acceptable excipient and endostatin protein having a molecular weight of approximately 18 kDa as determined by non-reducing gel electrophoresis, or approximately 20 kDa as determined by reducing gel electrophoresis, wherein the protein is a fragment of collagen that binds to a heparin affinity column and does not bind to a lysine affinity column, and wherein the protein inhibits proliferating cultured endothelial cells.

31. The composition of claim 30, wherein the endostatin protein has a N-terminal amino acid sequence shown in SEQ ID NO:1.

32. The composition of claim 30, wherein the endostatin protein has an amino acid sequence of a C-terminal peptide fragment of collagen type XVIII.

33. The composition of claim 30, wherein the endostatin protein has an amino acid sequence of a peptide fragment of collagen type XV.

34. The composition of claim 30, wherein the endostatin protein is made by a process comprising recombinantly producing the endostatin protein in a recombinant expression system, and isolating the recombinantly produced protein.

* * * * *

UNITED STATES PATENT AND TRADEMARK OFFICE
CERTIFICATE OF CORRECTION

PATENT NO. : 5,854,205

DATED : December 29, 1998

INVENTOR(S) : O'Reilly, et al.

It is certified that error appears in the above-identified patent and that said Letters Patent is hereby corrected as shown below:

Column 1, delete lines 4-7 and insert --This invention may have been made in part by funds from NIH grants RO1-CA64481 and PO1-CA45548. The U. S. government may have certain rights in this invention.--

Signed and Sealed this

Thirtieth Day of March, 1999

*Attest:*

Q. TODD DICKINSON

*Attesting Officer*   Acting Commissioner of Patents and Trademarks

UNITED STATES PATENT AND TRADEMARK OFFICE
CERTIFICATE OF CORRECTION

PATENT NO. : 5,854,205  
DATED : December 29, 1998  
INVENTOR(S) : O'Reilly, et al.

Page 1 of 3

It is certified that error appears in the above-identified patent and that said Letters Patent is hereby corrected as shown below:

Column 8,  
Lines 12-18, please delete the following two sentences,  
"The N-terminal amino acid sequence of endostatin to an internal 20 amino acid peptide fragment found in collagen alpha 1 type XVIII starting at amino acid 1105 and amino acid 1124. The N-terminal amino acid squence of the o corresponds to an internal 20 amino acid peptide fragment man collagen alpha type XVIII starting at amino acid 1132 at amino acid 1151."

And replace therefor the following two sentences:

-- The N-terminal amino acid sequence of endostatin corresponds to an internal 20 amino acid peptide fragment found in mouse collagen alpha type XVIII starting at amino acid 1105 and ending at amino acid 1124. The N-terminal amino acid sequence of the inhibitor also corresponds to an internal 20 amino acid peptide fragment found in human collagen alpha type 1 XVIII starting at amino acid 1132 and ending a amino acid 1151. --

Column 33,  
Line 37 of claim 1, please delete "collasen" and replace therefor with -- collagen --.

Signed and Sealed this

Twenty-seventh Day of November, 2001

*Attest:*

*Attesting Officer*

NICHOLAS P. GODICI  
*Acting Director of the United States Patent and Trademark Office*

UNITED STATES PATENT AND TRADEMARK OFFICE
CERTIFICATE OF CORRECTION

PATENT NO.  : 5,854,205
DATED       : December 29, 1998
INVENTOR(S) : O'Reilly, et al.

It is certified that error appears in the above-identified patent and that said Letters Patent is hereby corrected as shown below:

Please replace sheet 11 of 16 of the drawings with Figure 9 attached below.

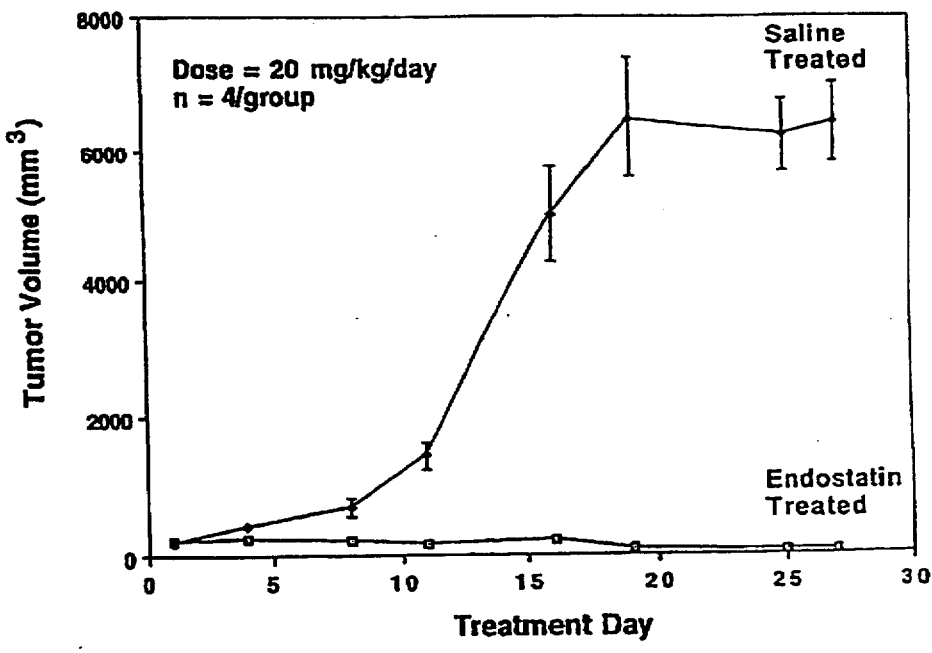

Figure 9

UNITED STATES PATENT AND TRADEMARK OFFICE
CERTIFICATE OF CORRECTION

PATENT NO. : 5,854,205
DATED : December 29, 1998
INVENTOR(S) : O'Reilly, et al.

It is certified that error appears in the above-identified patent and that said Letters Patent is hereby corrected as shown below:

Please replace sheet 12 of 16 of the drawings with Figure 10 attached below.

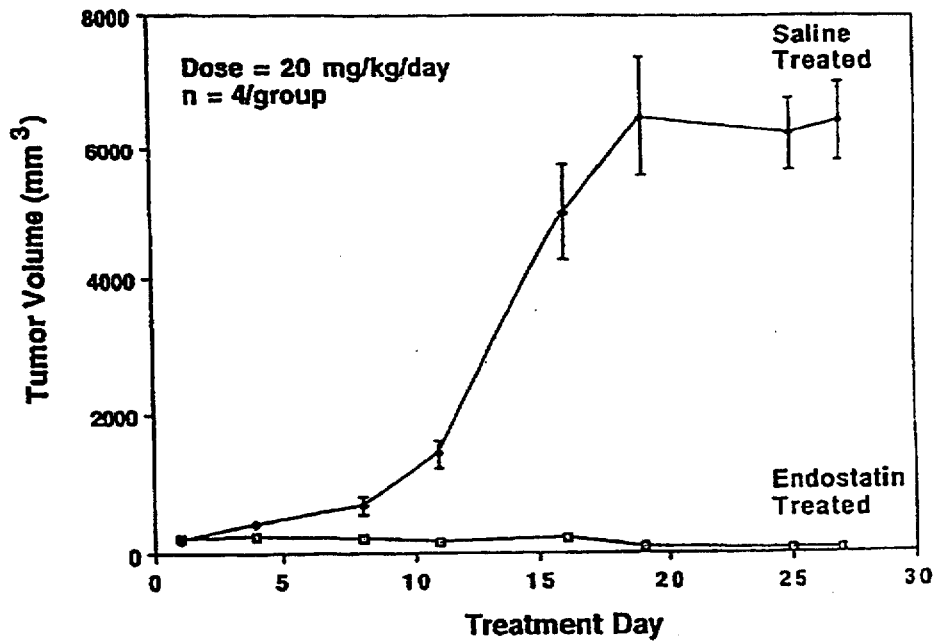

Figure 9

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Murine
        ( F ) TISSUE TYPE: Collagen (  x  i  ) SEQUENCE DESCRIPTION: SEQ ID NO:1:

| His | Thr | His | Gln | Asp | Phe | Gln | Pro | Val | Leu | His | Leu | Val | Ala | Leu | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Pro | Leu | Ser |
|-----|-----|-----|-----|
|     |     |     | 20  |

(  2  ) INFORMATION FOR SEQ ID NO:2:

(  i  ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (  i i  ) MOLECULE TYPE: protein (  i i i  ) HYPOTHETICAL: NO (  i v  ) ANTI-SENSE: NO (  v  ) FRAGMENT TYPE: internal (  v i  ) ORIGINAL SOURCE:
        ( A ) ORGANISM: Murine (  x i  ) SEQUENCE DESCRIPTION: SEQ ID NO:2:

| Met | Ala | Arg | Arg | Ala | Ser | Val | Gly | Thr | Asp |
|-----|-----|-----|-----|-----|-----|-----|-----|-----|-----|
| 1   |     |     |     | 5   |     |     |     |     | 10  |